United States Patent
Siegelmann et al.

(10) Patent No.: US 10,732,784 B2
(45) Date of Patent: Aug. 4, 2020

(54) SYSTEM AND METHODS FOR CUING VISUAL ATTENTION

(71) Applicant: University of Massachusetts, Boston, MA (US)

(72) Inventors: Hava T. Siegelmann, Boston, MA (US); Patrick Taylor, Boston, MA (US)

(73) Assignee: University of Massachusetts, Boston, MA (US)

(*) Notice: Subject to any disclaimer, the term of this patent is extended or adjusted under 35 U.S.C. 154(b) by 168 days.

(21) Appl. No.: 15/694,709

(22) Filed: Sep. 1, 2017

(65) Prior Publication Data
US 2018/0059875 A1 Mar. 1, 2018

Related U.S. Application Data

(60) Provisional application No. 62/382,539, filed on Sep. 1, 2016.

(51) Int. Cl.
| | |
|---|---|
| G06F 3/0481 | (2013.01) |
| G06F 3/0484 | (2013.01) |
| G06F 3/0487 | (2013.01) |
| G06F 3/01 | (2006.01) |
| G06T 11/00 | (2006.01) |
| A61B 3/113 | (2006.01) |
| G06F 17/00 | (2019.01) |

(52) U.S. Cl.
CPC ............ *G06F 3/0481* (2013.01); *G06F 3/013* (2013.01); *G06F 3/0487* (2013.01); *G06F 3/04812* (2013.01); *G06F 3/04842* (2013.01); *G06F 3/04845* (2013.01); *G06F 3/04847* (2013.01); *G06T 11/001* (2013.01); *A61B 3/113* (2013.01); *G06F 2203/04804* (2013.01)

(58) Field of Classification Search
CPC .... G06F 3/013; G06F 3/10481; G06F 3/0482; G06F 3/0485; G06F 3/0487; G06F 3/04847; A61B 3/113
See application file for complete search history.

(56) References Cited

U.S. PATENT DOCUMENTS

| | | |
|---|---|---|
| 6,401,050 B1 | 6/2002 | Cooke et al. |
| 2005/0073136 A1* | 4/2005 | Larsson ............. A61B 3/113 280/735 |
| 2005/0086610 A1 | 4/2005 | Mackinlay et al. |

(Continued)

OTHER PUBLICATIONS

"EyeFrame: real-time memory aid improves human multitasking via domain-general eye tracking procedures" by Taylor et al. Published 2015—total 33 pages (Year: 2015).*

(Continued)

*Primary Examiner* — Quoc A Tran
(74) *Attorney, Agent, or Firm* — Hamilton, Brook, Smith & Reynolds, P.C.

(57) ABSTRACT

A system and methods for cuing visual attention using one or more sensory cues. Sensory cues, such as visual and touch cues, are used to determine an area neglected by a user and presented on a screen display to cue the user to direct his/her attention to that neglected area. Sensory cues are independent of the program content—medical image, airplane pilot simulation, security x-ray pictures—conveyed on the screen display.

12 Claims, 13 Drawing Sheets

(56) References Cited

U.S. PATENT DOCUMENTS

| | | | | |
|---|---|---|---|---|
| 2011/0085700 | A1* | 4/2011 | Lee | G06Q 30/02 382/103 |
| 2014/0210978 | A1 | 7/2014 | Gunaratne et al. | |
| 2015/0042552 | A1* | 2/2015 | Tsoref | G06F 3/013 345/156 |
| 2016/0019801 | A1 | 1/2016 | Feerst | |
| 2016/0195924 | A1* | 7/2016 | Weber | G06F 3/0304 345/156 |
| 2018/0225509 | A1* | 8/2018 | Schmidt | G05B 19/0426 |

OTHER PUBLICATIONS

L. Fletcher et al, "Correlating driver gaze with the road scene for driver assistance systems", Robotics and Autonomous Systems, May 24, 2005.
GitLab Project Eye Frame file "EyeFrame.txt," File 1 of 2, published on the Internet Feb. 4, 2015, https://gitlab.com.
GitLab Project Eye Frame file "ClickThrough.java," File 1 of 2, published on the Internet Feb. 4, 2015, https://gitlab.com.
GitLab Project Eye Frame file "ComponentResizer.java," File 1 of 2, published on the Internet Feb. 4, 2015, https://gitlab.com.
GitLab Project Eye Frame file "Controller.java," File 1 of 2, published on the Internet Feb. 4, 2015, https://gitlab.com.
GitLab Project Eye Frame file "RunWindow.java," File 1 of 2, published on the Internet Feb. 4, 2015, https://gitlab.com.
GitLab Project Eye Frame file "Stack.java," File 1 of 2, published on the Internet Feb. 4, 2015, https://gitlab.com.
GitLab Project Eye Frame file "TrackerMain.java," File 1 of 2, published on the Internet Feb. 4, 2015. https://gitlab.com.
GitLab Project Eye Frame file "EyeFrame.txt," File 2 of 2, published on the Internet Feb. 4, 2015, https://gitlab.com.
GitLab Project Eye Frame file "ClickThrough.java," File 2 of 2, published on the Internet Feb. 4, 2015, https://gitlab.com.
GitLab Project Eye Frame file "Controller.java," File 2 of 2, published on the Internet Feb. 4, 2015, https://gitlab.com.
GitLab Project Eye Frame file "RunWindow.java," File 2 of 2, published on the Internet Feb. 4, 2015, https://gitlab.com.
GitLab Project Eye Frame file "TrackerMain.java," File 2 of 2, published on the Internet Feb. 4, 2015, https://gitlab.com.
GitLab Project Eye Frame file "EyeFrame.txt," published on the Internet Mar. 4, 2015, https://gitlab.com.
GitLab Project Eye Frame file "ClickThrough.java," published on the Internet Mar. 4, 2015, https://gitlab.com.
GitLab Project Eye Frame file "ComponentResizer.java," published on the Internet Mar. 4, 2015, https://gitlab.com.
GitLab Project Eye Frame file "Controller.java," published on the Internet Mar. 4, 2015, https://gitlab.com.
GitLab Project Eye Frame file "MainMenu.java," published on the Internet Mar. 4, 2015, https://gitlab.com.
GitLab Project Eye Frame file "RightClickMenu.java," published on the Internet Mar. 4, 2015, https://gitlab.com.
GitLab Project Eye Frame file "RunWindow.java," published on the Internet Mar. 4, 2015, https://gitlab.com.
GitLab Project Eye Frame file "Stack.java," published on the Internet Mar. 4, 2015, https://gitlab.com.
GitLab Project Eye Frame file "TrackerMain.java," published on the Internet Mar. 4, 2015, https://gitlab.com.
GitLab Project Eye Frame file "SWTResourceManager.java," published on the Internet Mar. 4, 2015, https://gitlab.com.
GitLab Project Eye Frame file "EyeFrame.txt," File 1 of 2, published on the Internet Feb. 6, 2015, https://gitlab.com.
GitLab Project Eye Frame file "ClickThrough.java," File 1 of 2, published on the Internet Feb. 6, 2015, https://gitlab.com.
GitLab Project Eye Frame file "ComponentResizer.java," File 1 of 2, published on the Internet Feb. 6, 2015, https://gitlab.com.
GitLab Project Eye Frame file "Controller.java," File 1 of 2, published on the Internet Feb. 6, 2015, https://gitlab.com.
GitLab Project Eye Frame file "RunWindow.java," File 1 of 2, published on the Internet Feb. 6, 2015, https://gitlab.com.
GitLab Project Eye Frame file "Stack.java," File 1 of 2, published on the Internet Feb. 6, 2015, https://gitlab.com.
GitLab Project Eye Frame file "TrackerMain.java," File 1 of 2, published on the Internet Feb. 6, 2015. https://gitlab.com.
GitLab Project Eye Frame file "EyeFrame.txt," File 2 of 2, published on the Internet Feb. 6, 2015, https://gitlab.com.
GitLab Project Eye Frame file "ClickThrough.java," File 2 of 2, published on the Internet Feb. 6, 2015, https://gitlab.com.
GitLab Project Eye Frame file "ComponentResizer.java," File 2 of 2, published on the Internet Feb. 6, 2015, https://gitlab.com.
GitLab Project Eye Frame file "Controller.java," File 2 of 2, published on the Internet Feb. 6, 2015, https://gitlab.com.
GitLab Project Eye Frame file "RunWindow.java," File 2 of 2, published on the Internet Feb. 6, 2015, https://gitlab.com.
GitLab Project Eye Frame file "Stack.java," File 2 of 2, published on the Internet Feb. 6, 2015, https://gitlab.com.
GitLab Project Eye Frame file "TrackerMain.java," File 2 of 2, published on the Internet Feb. 6, 2015, https://gitlab.com.
GitLab Project Eye Frame file "EyeFrame.txt," published on the Internet Mar. 6, 2015, https://gitlab.com.
GitLab Project Eye Frame file "ClickThrough.java," published on the Internet Mar. 6, 2015, https://gitlab.com.
GitLab Project Eye Frame file "ComponentResizer.java," published on the Internet Mar. 6, 2015, https://gitlab.com.
GitLab Project Eye Frame file "Controller.java," published on the Internet Mar. 6, 2015, https://gitlab.com.
GitLab Project Eye Frame file "MainMenu.java," published on the Internet Mar. 6, 2015, https://gitlab.com.
GitLab Project Eye Frame file "RightClickMenu.java," published on the Internet Mar. 6, 2015, https://gitlab.com.
GitLab Project Eye Frame file "RunWindow.java," published on the Internet Mar. 6, 2015, https://gitlab.com.
GitLab Project Eye Frame file "Stack.java," published on the Internet Mar. 6, 2015, https://gitlab.com.
GitLab Project Eye Frame file "TrackerMain.java," published on the Internet Mar. 6, 2015, https://gitlab.com.
GitLab Project Eye Frame file "SWTResourceManager.java," published on the Internet Mar. 6, 2015, https://gitlab.com.
GitLab Project Eye Frame file "EyeFrame.txt," File 1 of 2, published on the Internet Apr. 10, 2015, https://gitlab.com.
GitLab Project Eye Frame file "ClickThrough.java," File 1 of 2, published on the Internet Apr. 10, 2015, https://gitlab.com.
GitLab Project Eye Frame file "ComponentResizer.java," File 1 of 2, published on the Internet Apr. 10. 2015, https://gitlab.com.
GitLab Project Eye Frame file "Controller.java," File 1 of 2, published on the Internet Apr. 10, 2015, https://gitlab.com.
GitLab Project Eye Frame file "MainMenu.java," File 1 of 2, published on the Internet Apr. 10, 2015, https://gitlab.com.
GitLab Project Eye Frame file "RightClickMenu.java," File 1 of 2, published on the Internet Apr. 10, 2015, https://gitlab.com.
GitLab Project Eye Frame file "RunWindow.java," File 1 of 2, published on the Internet Apr. 10, 2015, https://gitlab.com.
GitLab Project Eye Frame file "ScaleMenu.java," File 1 of 2, published on the Internet Apr. 10, 2015, https://gitlab.com.
GitLab Project Eye Frame file "Stack.java," File 1 of 2, published on the Internet Apr. 10, 2015, https://gitlab.com.
GitLab Project Eye Frame file "TrackerMain.java," File 1 of 2, published on the Internet Apr. 10, 2015, https://gitlab.com.
GitLab Project Eye Frame file "Weighting.java," File 1 of 2, published on the Internet Apr. 10, 2015, https://gitlab.com.
GitLab Project Eye Frame file "SWTResourceManager.java," File 1 of 2, published on the Internet Apr. 10, 2015, https://gitlab.com.
GitLab Project Eye Frame file "EyeFrame.txt," File 2 of 2, published on the Internet Apr. 10, 2015, https://gitlab.com.
GitLab Project Eye Frame file "ClickThrough.java," File 2 of 2, published on the Internet Apr. 10, 2015, https://gitlab.com.
GitLab Project Eye Frame file "ComponentResizer.java," File 2 of 2, published on the Internet Apr. 10, 2015, https://gitlab.com.
GitLab Project Eye Frame file "Controller.java," File 2 of 2, published on the Internet Apr. 10, 2015, https://gitlab.com.
GitLab Project Eye Frame file "MainMenujava," File 2 of 2, published on the Internet Apr. 10, 2015, https://gitlab.com.

(56) References Cited

OTHER PUBLICATIONS

GitLab Project Eye Frame file "RightClickMenu.java," File 2 of 2, published on the Internet Apr. 10, 2015, https://gitlab.com.
GitLab Project Eye Frame file "RunWindow.java," File 2 of 2, published on the Internet Apr. 10, 2015, https://gitlab.com.
GitLab Project Eye Frame file "ScaleMenu.java," File 2 of 2, published on the Internet Apr. 10, 2015, https://gitlab.com.
GitLab Project Eye Frame file "Stack.java," File 2 of 2, published on the Internet Apr. 10, 2015, https://gitlab.com.
GitLab Project Eye Frame file "TrackerMain.java," File 2 of 2, published on the Internet Apr. 10, 2015, https://gitlab.com.
GitLab Project Eye Frame file "Weighting.java," File 2 of 2, published on the Internet Apr. 10, 2015, https://gitlab.com.
GitLab Project Eye Frame file "SWTResourceManager.java," File 2 of 2, published on the Internet Apr. 10, 2015, https://gitlab.com.
GitLab Project Eye Frame file "EyeFrame.txt," published on the Internet Mar. 11, 2015, https://gitlab.com.
GitLab Project Eye Frame file "ClickThrough.java," published on the Internet Mar. 11, 2015, https://gitlab.com.
GitLab Project Eye Frame file "ComponentResizer.java," published on the Internet Mar. 11, 2015, https://gitlab.com.
GitLab Project Eye Frame file "Controller.java," published on the Internet Mar. 11, 2015, https://gitlab.com.
GitLab Project Eye Frame file "MainMenu.java," published on the Internet Mar. 11, 2015, https://gitlab.com.
GitLab Project Eye Frame file "RightClickMenu.java," published on the Internet Mar. 11, 2015, https://gitlab.com.
GitLab Project Eye Frame file "RunWindow.java," published on the Internet Mar. 11, 2015, https://gitlab.com.
GitLab Project Eye Frame file "Stack.java," published on the Internet Mar. 11, 2015, https://gitlab.com.
GitLab Project Eye Frame file "TrackerMain.java," published on the Internet Mar. 11, 2015, https://gitlab.com.
GitLab Project Eye Frame file "SWTResourceManager.java," published on the Internet Mar. 11, 2015, https://gitlab.com.
GitLab Project Eye Frame file "EyeFrame.txt," published on the Internet Feb. 13, 2015, https://gitlab.com.
GitLab Project Eye Frame file "ClickThrough.java," published on the Internet Feb. 13, 2015, https://gitlab.com.
GitLab Project Eye Frame file "ComponentResizer.java," published on the Internet Feb. 13, 2015, https://gitlab.com.
GitLab Project Eye Frame file "Controller.java," published on the Internet Feb. 13, 2015, https://gitlab.com.
GitLab Project Eye Frame file "RunWindow.java," published on the Internet Feb. 13, 2015, https://gitlab.com.
GitLab Project Eye Frame file "Stack.java," published on the Internet Feb. 13, 2015, https://gitlab.com.
GitLab Project Eye Frame file "TrackerMain.java," published on the Internet Feb. 13, 2015, https://gitlab.com.
GitLab Project Eye Frame file "EyeFrame.txt," published on the Internet Apr. 15, 2015, https://gitlab.com.
GitLab Project Eye Frame file "ClickThrough.java," published on the Internet Apr. 15, 2015, https://gitlab.com.
GitLab Project Eye Frame file "ClickThroughComparable.java," published on the Internet Apr. 15, 2015, https://gitlab.com.
GitLab Project Eye Frame file "ComponentResizer.java," published on the Internet Apr. 15, 2015, https://gitlab.com.
GitLab Project Eye Frame file "Controller.java," published on the Internet Apr. 15, 2015, https://gitlab.com.
GitLab Project Eye Frame file "MainMenu.java," published on the Internet Apr. 15, 2015, https://gitlab.com.
GitLab Project Eye Frame file "RightClickMenu.java," published on the Internet Apr. 15, 2015, https://gitlab.com.
GitLab Project Eye Frame file "RunWindow.jaya," published on the Internet Apr. 15, 2015, https://gitlab.com.
GitLab Project Eye Frame file "ScaleMenu.java," published on the Internet Apr. 15, 2015, https://gitlab.com.
GitLab Project Eye Frame file "Stack.java," published on the Internet Apr. 15, 2015, https://gitlab.com.
GitLab Project Eye Frame file "TrackerMain.java," published on the Internet Apr. 15, 2015, https://gitlab.com.
GitLab Project Eye Frame file "Weighting.java," published on the Internet Apr. 15, 2015, https://gitlab.com.
GitLab Project Eye Frame file "WeightScale.java," published on the Internet Apr. 15, 2015, https://gitlab.com.
GitLab Project Eye Frame file "SWTResourceManager.java," published on the Internet Apr. 15, 2015, https://gitlab.com.
GitLab Project Eye Frame file "EyeFrame.txt," File 1 of 2, published on the Internet Feb. 17, 2015, https://gitlab.com.
GitLab Project Eye Frame file "ClickThrough.java," File 1 of 2, published on the Internet Feb. 17, 2015, https://gitlab.com.
GitLab Project Eye Frame file "ComponentResizer.java," File 1 of 2, published on the Internet Feb. 17, 2015, https://gitlab.com.
GitLab Project Eye Frame file "Controller.java," File 1 of 2, published on the Internet Feb. 17, 2015, https://gitlab.com.
GitLab Project Eye Frame file "RightClickMenu.java," File 1 of 2, published on the Internet Feb. 17, 2015, https://gitlab.com.
GitLab Project Eye Frame file "RunWindow.java," File 1 of 2, published on the Internet Feb. 17, 2015, https://gitlab.com.
GitLab Project Eye Frame file "Stack.java," File 1 of 2, published on the Internet Feb. 17, 2015, https://gitlab.com.
GitLab Project Eye Frame file "TrackerMain.java," File 1 of 2, published on the Internet Feb. 17, 2015, https://gitlab.com.
GitLab Project Eye Frame file "EyeFrame.txt," File 2 of 2, published on the Internet Feb. 17, 2015, https://gitlab.com.
GitLab Project Eye Frame file "ClickThrough.java," File 2 of 2, published on the Internet Feb. 17, 2015, https://gitlab.com.
GitLab Project Eye Frame file "ComponentResizer.java," File 2 of 2, published on the Internet Feb. 17, 2015, https://gitlab.com.
GitLab Project Eye Frame file "Controller.java," File 2 of 2, published on the Internet Feb. 17, 2015, https://gitlab.com.
GitLab Project Eye Frame file "RunWindow.java," File 2 of 2, published on the Internet Feb. 17, 2015, https://gitlab.com.
GitLab Project Eye Frame file "Stack.java," File 2 of 2, published on the Internet Feb. 17, 2015, https://gitlab.com.
GitLab Project Eye Frame file "TrackerMain.java," File 2 of 2, published on the Internet Feb. 17, 2015, https://gitlab.com.
GitLab Project Eye Frame file "EyeFrame.txt," published on the Internet Mar. 23, 2015, https://gitlab.com.
GitLab Project Eye Frame file "ClickThrough.java," published on the Internet Mar. 23, 2015, https://gitlab.com.
GitLab Project Eye Frame file "ComponentResizer.java," published on the Internet Mar. 23, 2015, https://gitlab.com.
GitLab Project Eye Frame file "Controller.java," published on the Internet Mar. 23, 2015, https://gitlab.com.
GitLab Project Eye Frame file "MainMenu.java," published on the Internet Mar. 23, 2015, https://gitlab.com.
GitLab Project Eye Frame file "RightClickMenu.java," published on the Internet Mar. 23, 2015, https://gitlab.com.
GitLab Project Eye Frame file "RunWindow.java," published on the Internet Mar. 23, 2015, https://gitlab.com.
GitLab Project Eye Frame file "ScaleMenu.java," published on the Internet Mar. 23, 2015, https://gitlab.com.
GitLab Project Eye Frame file "Stack.java," published on the Internet Mar. 23, 2015, https://gitlab.com.
GitLab Project Eye Frame file "TrackerMain.java," published on the Internet Mar. 23, 2015, https://gitlab.com.
GitLab Project Eye Frame file "SWTResourceManager.java," published on the Internet Mar. 23, 2015, https://gitlab.com.
GitLab Project Eye Frame file "EyeFrame.txt," published on the Internet Mar. 24, 2015, https://gitlab.com.
GitLab Project Eye Frame file "ClickThrough.java," published on the Internet Mar. 24, 2015, https://gitlab.com.
GitLab Project Eye Frame file "ComponentResizer.java," published on the Internet Mar. 24, 2015, https://gitlab.com.
GitLab Project Eye Frame file "Controller.java," published on the Internet Mar. 24, 2015, https://gitlab.com.
GitLab Project Eye Frame file "MainMenu.java," published on the Internet Mar. 24, 2015, https://gitlab.com.
GitLab Project Eye Frame file "RightClickMenu.java," published on the Internet Mar. 24, 2015, https://gitlab.com.

(56) References Cited

OTHER PUBLICATIONS

GitLab Project Eye Frame file "RunWindow.java," published on the Internet Mar. 24, 2015, https://gitlab.com.
GitLab Project Eye Frame file "ScaleMenu.java," published on the Internet Mar. 24, 2015, https://gitlab.com.
GitLab Project Eye Frame file "Stack.java," published on the Internet Mar. 24, 2015, https://gitlab.com.
GitLab Project Eye Frame file "TrackerMain.java," published on the Internet Mar. 24, 2015, https://gitlab.com.
GitLab Project Eye Frame file "Weighting.java," published on the Internet Mar. 24, 2015, https://gitlab.com.
GitLab Project Eye Frame file "SWTResourceManager.java," published on the Internet Mar. 24, 2015, https://gitlab.com.
GitLab Project Eye Frame file "EyeFrame.txt," published on the Internet Feb. 26, 2015, https://gitlab.com.
GitLab Project Eye Frame file "ClickThrough.java," published on the Internet Feb. 26, 2015, https://gitlab.com.
GitLab Project Eye Frame file "ComponentResizer.java," published on the Internet Feb. 26, 2015, https://gitlab.com.
GitLab Project Eye Frame file "Controller.java," published on the Internet Feb. 26, 2015, https://gitlab.com.
GitLab Project Eye Frame file "RightClickMenu.java," published on the Internet Feb. 26, 2015, https://gitlab.com.
GitLab Project Eye Frame file "RunWindow.java," published on the Internet Feb. 26, 2015, https://gitlab.com.
GitLab Project Eye Frame file "Stack.java," published on the Internet Feb. 26, 2015, https://gitlab.com.
GitLab Project Eye Frame file "TrackerMain.java," published on the Internet Feb. 26, 2015, https://gitlab.com.
GitLab Project Eye Frame file "EyeFrame.txt," published on the Internet Mar. 27, 2015, https://gitlab.com.
GitLab Project Eye Frame file "ClickThrough.java," published on the Internet Mar. 27, 2015, https://gitlab.com.
GitLab Project Eye Frame file "ComponentResizer.java," published on the Internet Mar. 27, 2015, https://gitlab.com.
GitLab Project Eye Frame file "Controller.java," published on the Internet Mar. 27, 2015, https://gitlab.com.
GitLab Project Eye Frame file "MainMenu.java," published on the Internet Mar. 27, 2015, https://gitlab.com.
GitLab Project Eye Frame file "RightClickMenu.java," published on the Internet Mar. 27, 2015, https://gitlab.com.
GitLab Project Eye Frame file "RunWindow.java," published on the Internet Mar. 27, 2015, https://gitlab.com.
GitLab Project Eye Frame file "ScaleMenu.java," published on the Internet Mar. 27, 2015, https://gitlab.com.
GitLab Project Eye Frame file "Stack.java," published on the Internet Mar. 27, 2015, https://gitlab.com.
GitLab Project Eye Frame file "TrackerMain.java," published on the Internet Mar. 27, 2015, https://gitlab.com.
GitLab Project Eye Frame file "Weighting.java," published on the Internet Mar. 27, 2015, https://gitlab.com.
GitLab Project Eye Frame file "SWTResourceManager.java," published on the Internet Mar. 27, 2015, https://gitlab.com.
GitLab Project Eye Frame file "EyeFrame.txt," published on the Internet Jan. 28, 2015, https://gitlab.com.
GitLab Project Eye Frame file "ClickThrough.java," published on the Internet Jan. 28, 2015, https://gitlab.com.
GitLab Project Eye Frame file "Controller.java," published on the Internet Jan. 28, 2015, https://gitlab.com.
GitLab Project Eye Frame file "RunWindow.java," published on the Internet Jan. 28, 2015, https://gitlab.com.
GitLab Project Eye Frame file "TrackerMain.java," published on the Internet Jan. 28, 2015, https://gitlab.com.
GitLab Project Eye Frame file "EyeFrame.txt," File 1of 3, published on the Internet Jan. 30, 2015, https://gitlab.com.
GitLab Project Eye Frame file "ClickThrough.java," File 1of 3, published on the Internet Jan. 30, 2015, https://gitlab.com.
GitLab Project Eye Frame file "Controller.java," File 1of 3, published on the Internet Jan. 30, 2015, https://gitlab.com.
GitLab Project Eye Frame file "RunWindow.java," File 1of 3, published on the Internet Jan. 30, 2015, https://gitlab.com.
GitLab Project Eye Frame file "TrackerMain.java," File 1of 3, published on the Internet Jan. 30, 2015, https://gitlab.com.
GitLab Project Eye Frame file "EyeFrame.txt," File 2 of 3, published on the Internet Jan. 30, 2015, https://gitlab.com.
GitLab Project Eye Frame file "ClickThrough.java," File 2of 3, published on the Internet Jan. 30, 2015, https://gitlab.com.
GitLab Project Eye Frame file "Controller.java," File 2 of 3, published on the Internet Jan. 30, 2015, https://gitlab.com.
GitLab Project Eye Frame file "RunWindow.java," File 2 of 3, published on the Internet Jan. 30, 2015, https://gitlab.com.
GitLab Project Eye Frame file "TrackerMain.java," File 2 of 3, published on the Internet Jan. 30, 2015, https://gitlab.com.
GitLab Project Eye Frame file "EyeFrame.txt," File 3 of 3, published on the Internet Jan. 30, 2015, https://gitlab.com.
GitLab Project Eye Frame file "ClickThrough.java," File 3of 3, published on the Internet Jan. 30, 2015, https://gitlab.com.
GitLab Project Eye Frame file "Controller.java," File 3 of 3, published on the Internet Jan. 30, 2015, https://gitlab.com.
GitLab Project Eye Frame file "RunWindow.java," File 3 of 3, published on the Internet Jan. 30, 2015, https://gitlab.com.
GitLab Project Eye Frame file "TrackerMain.java," File 3 of 3, published on the Internet Jan. 30, 2015, https://gitlab.com.
Taylor, P., et al., "Human strategies for multitasking, search, and control improved via real-time memory aid for gaze location"; Frontiers in ICT; Sep. 7, 2015; (22 pages).

\* cited by examiner

SYSTEM AND METHODS FOR CUING VISUAL ATTENTION

CROSS-REFERENCE TO RELATED APPLICATIONS

This application claims priority to U.S. Provisional Patent Application Ser. No. 62/382,539 filed Sep. 1, 2016.

FEDERALLY-SPONSORED RESEARCH OR DEVELOPMENT

This invention is made with government support under N00014-09-1-0069 awarded by the Office of Naval Research. The government has certain rights in the invention.

FIELD OF THE INVENTION

The invention relates generally to a system and methods for cuing visual attention. More specifically, the invention relates to a system and methods that uses attention input data, for example characteristics of an individual's gaze on a display or location of a cursor correlated to a mouse input device, to cue visual attention to an area of a screen display that is neglected by the individual. Advantageously, an individual may more easily manage visual attention to information on one or more areas.

BACKGROUND

The vast majority of people are poor multitaskers. To make matters worse, some of those who score worst on measures of multitasking performance tend to perceive that they are better at multitasking, with a negative correlation between perception and ability in large studies. These issues are particularly important, since in every day work-life, multitasking may often be necessary or efficient for a variety of human labor. Multitasking is directed to the cognitive process of concentrating on a specific sensory stimulus (i.e., attention to the stimulus).

A job may require an individual to direct attention to multiple tasks given the individual's responsibilities. For example, an individual may be required to view displays on several monitors and focus on certain information. However, the individual may neglect viewing one or more displays or areas on some displays and miss some information.

Interactions with partially autonomous processes are becoming an integral part of human industrial and civil function. Given semi-autonomy, many such tasks can often be monitored by a user at one time. In the course of operating a computer or vehicle, a single human might manage multiple processes, e.g., search and rescue type mobile robots, performing medical supply distribution, patient checkup, general cleanup, firefighting tasks, as well as process control with many dials or readings, security or surveillance monitoring, or other forms of human-based monitoring or tracking tasks. Generally, each automated agent or process only needs intermittent supervision and guidance from a human to optimize performance, and thus a single user can remotely operate or supervise multiple entities, for efficiency of labor. When controlling multiple automated processes at once, the user must decide how to distribute attention across each task. Even if the operator conducts the same type of task with each automated process, this form of human-system interaction requires a multitasking effort.

Unfortunately, most people are notoriously poor multitaskers and can remain unaware of visually subtle cues that indicate the need for user input. Further complicating the situation, individuals who perform worst at multitasking actually perceive they are better at multitasking, demonstrated by negative correlations between ability and perception of ability in large studies. To make matters worse, humans often naturally develop a plethora of biases of attention and perception. To address many of these issues, divided attention performance has been studied for many years. A further difficulty in multitasking is that brains rely heavily upon prediction and, fundamentally, are incapable of knowing what important information they have missed.

Eye tracking to ascertain point of gaze is a highly effective method of determining where people orient their attention, as well as what they deem important. Traditionally, eye tracking informed post-experiment analysis, rather than helping users in the field in real-time. For example, a study might analyze optimal gaze strategies in high-performing groups, and then at a later date, train new users on those previously discovered optimal search strategies. For example, studies have trained novice drivers' gaze to mimic experienced drivers with lower crash risk.

Alternatively, eye movement strategies can be employed to optimize real-time task performance, since many eye-movements are capable of being intentionally controlled. For those eye movements that cannot easily be intentionally controlled, salient "pop-out" cues (e.g., flashing red box around target) can reliably direct attention in a more automatic, bottom-up manner. As we discuss further, many eye tracking systems have been developed for real-time control, with very few attempting pure assistance, though none were both successful and domain-general. Hence there is a need for such an assistive system.

Tracking a participant's eye movements while multitasking is an especially good way to glean optimal cognitive strategies. Much work has shown that eye tracking to determine point of gaze can reliably convey the location at which humans' visual attention is currently directed. Locus of attention is a factor that can illustrate which of multiple tasks a participant is currently attending to, as well as many other details. Further, measuring where humans look tends to be highly informative of what is interesting to them in a particular scene, and can be helpful for inferring cognitive strategies. Generally, gaze appears deeply intertwined with cognitive processes.

Multitasking principles also apply when managing multiple items in working memory. For working memory, another cognitive construct that is difficult to measure and discussed at length below, eye movement paradigms have revealed how visual search tasks can be interfered with when working memory is being taxed.

Though many paradigms have been developed to study multitasking using eye tracking, most traditional applications of eye tracking are not used in real time, but instead to augment training, or simply to observe optimal strategies. For an example of training, post-experiment analysis of gaze data can be used to determine an attention strategy of the best-performing participants or groups. Then, these higher-performing strategies can be taught during training sessions at a later date. Implemented examples include educating health care professionals on visual scanning patterns associated with reduced incidence of medical documentation errors, and training novice drivers' gaze behaviors to mimic more experienced drivers with lower crash risk. As eye tracking methods become more popular, they have been applied in the field of human-computer interaction and usability, as well as human-robot interaction, though in this area, guiding principles for optimal gaze strategies are still nascent.

Real-time reminders for tasks can improve user performance. Generally, real-time cuing of goals can speed or increase the accuracy of detection. Highlighting display elements in a multi-display may assist in directing attention, though eye tracking may often be critical to reliably automate such reminders for many tasks. As described above, there is little previous work developing real-time eye tracking assistance, with most research focused on training, evaluation, or basic hypothesis testing. The real-time systems developed previously are lacking in domain-generality, utility, and flexibility. There is a need for an assistive system and methods for managing multiple visual tasks, which is domain-general, transparent, intuitive, non-interfering, non-command, improves control (without replacing direct control), and adaptively extrapolates to a variety of circumstances.

Visual attention of the individual may be inferred from measuring the location of an individual's gaze on a display, for example, a graphical user interface on a monitor. Various technologies exist for measuring the location of an individual's gaze and attention. A mouse cursor location may be used as an implicit measurement of attention. For example, a software program may be operated to identify the location of a digital cursor on a graphical user interface positioned by a mouse and by implication an individual's gaze. Also, an optical sensor may measure the location or duration of an individual's gaze. For example, a software program may calculate a vector between a pupil center and a corneal reflection to determine the location of an individual's gaze.

Eye-tracking systems measure the location of an individual's gaze on a display to determine whether the individual's visual attention is directed on a certain area. Some conventional eye-tracking systems determine whether the individual's visual attention is directed to specific content in a certain area on the display. Hence these systems are dependent on the content displayed on the screen. Other eye-tracking systems only provide a visual cue, such as show a "warning", to direct an individual's visual attention. There is a need for a system and methods to provide a cue to direct visual attention to an area independent of the content conveyed on the screen display.

The invention solves the above recognized needs by providing a system and methods for providing sensory cue to direct visual attention to an area neglected by an individual's gaze.

SUMMARY OF THE INVENTION

The invention is a system and methods for cuing visual attention. Advantageously, the invention may facilitate better management of an individual's visual attention to one or more areas of a screen display independent of the program content conveyed or queued to be conveyed on the screen display: the invention may be used with medical imaging software, airplane pilot simulator software, security x-ray software, etc.

According to the invention, the system may include one or more input devices, sensors, computer processors, and output devices. In certain preferred embodiments, the system permits a user to select a display including one or more areas with at least one of the input devices. The one or more sensors, such as a camera, eye-tracking device, touch sensor, and/or mouse, collect data from measurements of an individual's gaze or touch (e.g., finger or mouse). At least one of the computer processors analyzes the attention input data to determine if an individual's gaze/touch has neglected one or more areas for one or more periods of time and at least one of the output devices provides a sensory cue to direct visual attention to the one or more areas an individual's gaze has neglected for a period of time.

In preferred embodiments, the system is configured for cuing visual attention. A user initiates a software program stored on non-transitory computer readable medium so that the user may select one or more displays, such as a graphical user interface on a monitor, with one or more areas each defined by a size, shape, and location on the one or more displays. The user chooses one or more periods of time within which an individual's measured attention must be on the one or more areas. The user chooses one or more sensory cues to direct visual attention to the one or more areas which have been neglected by the individual's attention.

In certain embodiments, the system may be configured so that multiple sensors will measure an individual's attention. In certain preferred embodiments, the system may include sensors of the same type, for example, two or more optical sensors. In certain preferred embodiments, the system may include sensors of different types, for example, a mouse and an optical sensor.

In certain embodiments, the system may be configured so that the output device provides a sensory cue. The sensory cue may be visual and/or audible. In certain preferred embodiments, a visible sensory cue may include a change in color, hue, pattern, and/or shape. In some embodiments, a visible sensory cue may include a border around an area. In some embodiments, an audible sensory cue may include a certain sound, for example, sounds directing an individual to gaze at a specific display.

In certain preferred embodiments, a display may be a graphical user interface on a monitor. In some embodiments, the display may be a dashboard. In some embodiments, the display may be a windshield. In some embodiments, the display may include at least one area configured to have a different importance than at least one other area. For example, an area with a higher importance may have a shorter period of time within which an individual must gaze at the area before a sensory cue is provided. In some embodiments, the importance of an area may change after the occurrence of a trigger event which may be configured by a user. For example, a user may configure one area's importance to increase after an individual looks at a different area.

Attention of a user to one or more areas of a display screen is measured to determine whether one or more areas have been neglected. Attention may be measured by the individual's gaze or controlled movement of an input device. A sensory cue may be dependent on whether a specific individual's gaze has not been at an area within a period of time. Furthermore, a sensory cue may be dependent on whether multiple individuals' gazes have not been at an area within a period of time.

According to the invention, both a programming phase and an execution phase are provided for using one or more sensory cue to direct visual attention on a screen display. During a programming phase, an area on a screen display where attention will be measured is defined. Sensory cues are programmed to estimate attention. Parameters define sensory cues such as size, shape, color, overlay, etc. A user interface is accessed to define settings for each sensory cue. The user interface is used to enter a minimum time threshold. The minimum time threshold is the minimum time a user must pay attention to an area of a screen. The time a user pays attention to a particular area of a screen is determined by use of an input device. The input device is used for acquiring attention input data, for example, a cursor within an area as directed by the mouse input device controlled by a user or eye gaze within the region or frame as recorded by an eye tracker device. Each sensory cue defines an area of the display screen and serves as an activation cue to direct the individual's attention.

During execution, if a user does not pay attention to an area that meets the minimum time threshold, data is not accepted. If the attention input data recorded real-time meets the minimum time threshold, then the data is accepted and used to update in real-time a number of accepted attention input data. The sensory cue not only defines an area of the display screen for recording and accepting attention input data to determine a neglected area of a screen display, but is also used to present on the screen display to cue the user to direct their attention to that neglected area. In order to determine if an area of the screen display is neglected, all numbers that total the accepted input data of each sensory cue are compared real-time. The sensory cue with the longest duration of time attention input data was recorded within the frame as compared to other frames is assigned a neglected status. The most neglected frame is that with the largest time since last attended to, and the second most neglected frame is that with the second longest time internal since it was last attended to based on the accepted data. All other frames are considered normal or regular. In other words, the frame with the longest time since last accepted data of attention in comparison to all frames is the most neglected frame. The associated area—an activation cue—is displayed on the screen according to the parameters selected during a programming phase.

The invention and its attributes and advantages may be further understood and appreciated with reference to the detailed description below of one contemplated embodiment, taken in conjunction with the accompanying drawings.

BRIEF DESCRIPTION OF THE DRAWINGS

Embodiments are illustrated by way of example and not limitation in the figures in the accompanying drawings, in which like references indicate similar elements and in which.

DETAILED DESCRIPTION OF EMBODIMENTS OF THE INVENTION

The invention is directed to a system and methods for providing one or more sensory cues to direct visual attention. A user's gaze on a screen display is monitored. Once it is determined that the user's gaze is neglecting an area of the screen display, a sensory cue prompts the user to direct their visual attention to that area of the screen display. For purposes of this invention, the sensory cue is a visual cue but any sensory cue is contemplated such as an audible cue or tactile cue.

The invention is directed to an application for selecting or creating sensory cues, using the sensory cues to record attention input data to determine a neglected area of a screen display, and presenting the sensory cue to cue the user to direct their attention to that area of the screen display.

According to the invention, there are two phases of the application that provide one or more sensory cues to direct visual attention: a sensory cue programming phase and a sensory cue execution phase. Sensory cues are selected or created during the sensory cue programming phase. During the execution phase, the sensory cues are used to determine areas neglected from a user's attention and are further presented on the screen display as an activation cue to direct the user's attention to that area.

The drawings and description are directed to a particular embodiment of the invention directed to a sensory cue in the form of a visual cue, otherwise referred to as an activation cue. More specifically, the visual cue is in the form of a frame component defining an area or region. The frame component comprises a window element and a border element, but any form of visual cue is contemplated. For example, the visual cue could be any shape, size, or transparency. During an execution phase, the frames are used to determine if a user is neglecting one or more areas of the screen display. The frame component is illustrated according to programmed parameters on the screen display to direct visual attention. Advantageously, the invention operates with no dependency on the program content conveyed or queued to be conveyed on the screen display: the invention may be used with medical imaging software, airplane pilot simulator software, security x-ray software, etc. Hence the method is independent of the underlying application and data, and can be used to reach optimal performance.

Figure 12:
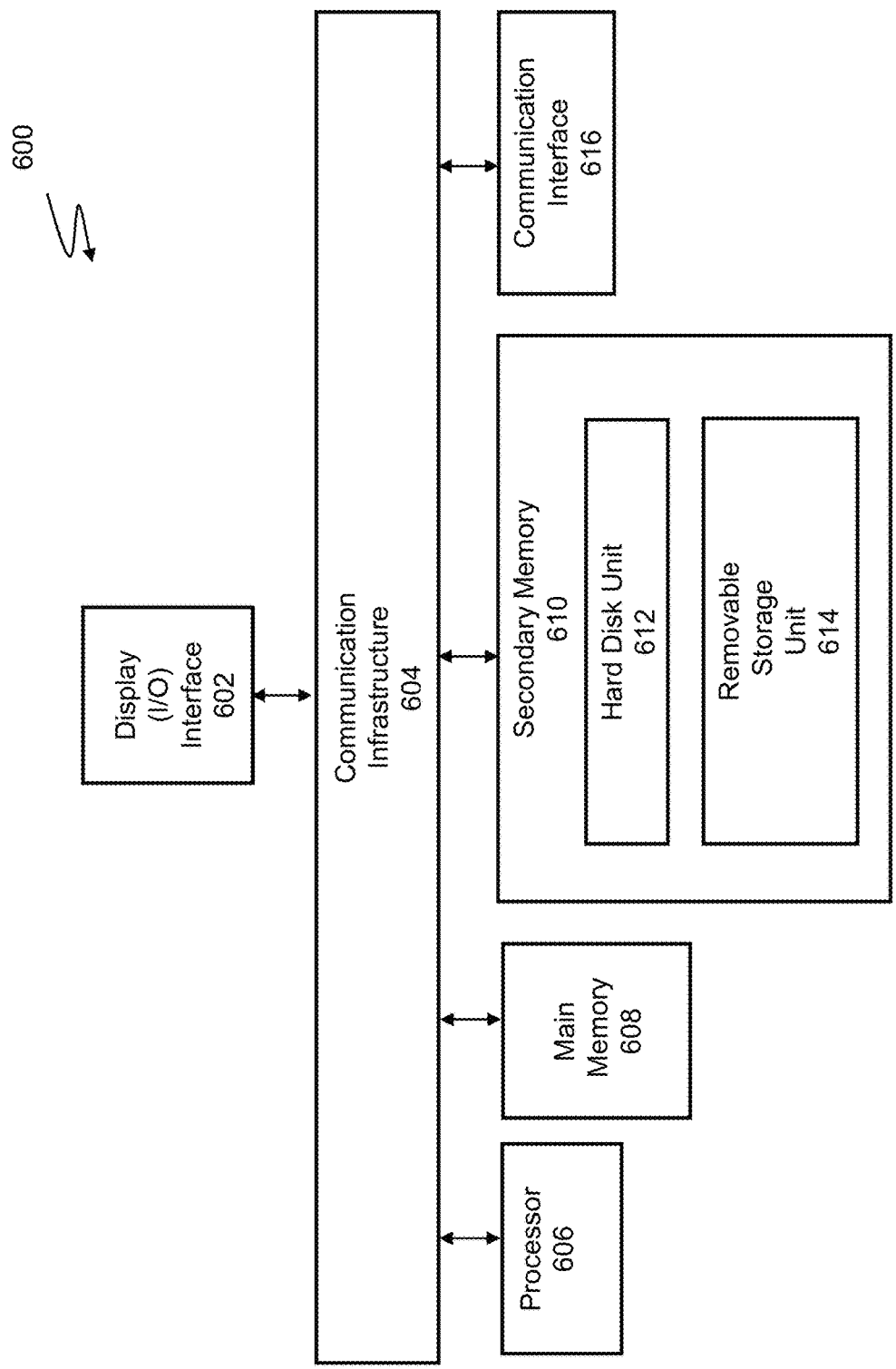
FIG. 12 illustrates a computer system that may be used to implement the methods according to the invention.
Figure 13:
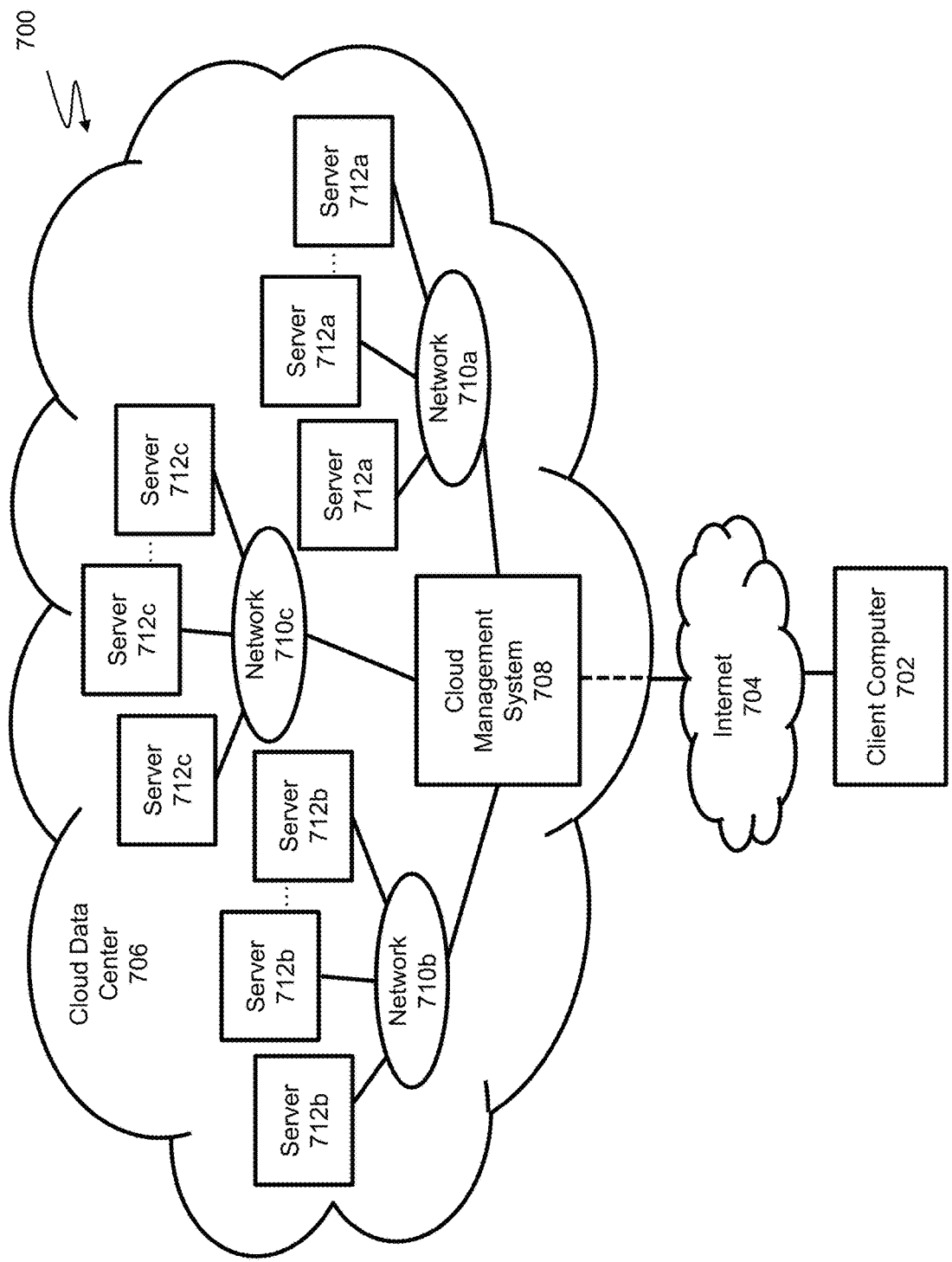
FIG. 13 illustrates a cloud computing system that may be used to implement the methods according to the invention.

The programming phase of the invention is described and detailed in FIGS. 1-7. The execution phase is described and detailed in FIGS. 8-11. FIGS. 12-13 are exemplary systems that may be used to implement the phases of the invention.

Figure 1:
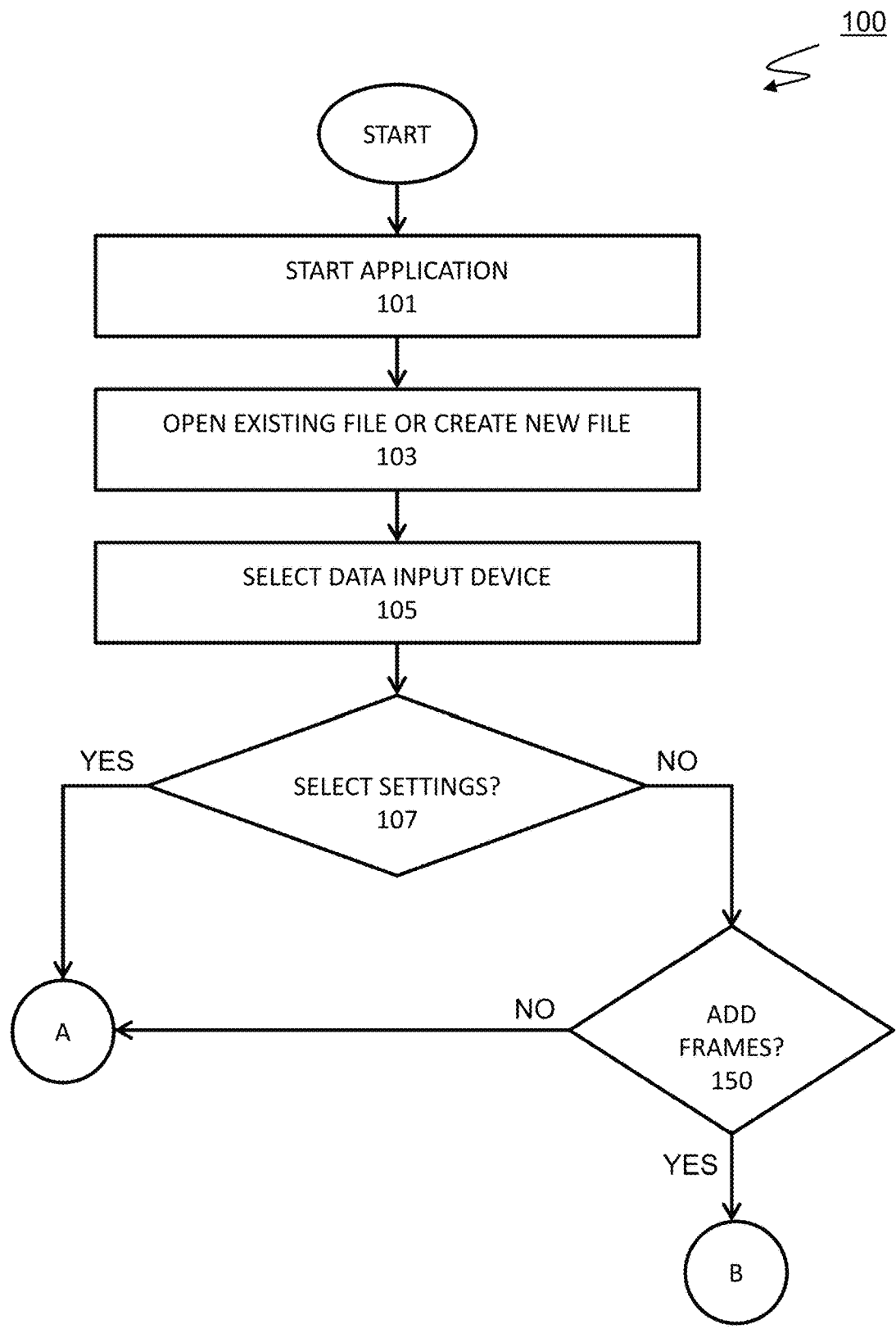
FIG. 1 illustrates a flow chart of method steps performed during a programming phase of the application.

FIG. 1 illustrates a flow chart 100 of method steps performed during a programming phase of the application. The method of FIG. 1 may be implemented using the user interface 500 shown in FIG. 2.

As shown in FIG. 1, the programming phase of the application begins at step 101. At step 103, either an existing file of frames is selected or a new file of frames is created. The input device selected is shown at step 105. The input device is any device that can be used to provide attention input data, for example, a computer mouse, a touch screen, a touch pad, a stylus, a keyboard. Settings for the frames may then be selected at step 107. If settings are not selected at step 107, a new file of frames may be created at step 150 (see FIG. 6).

Figure 2:
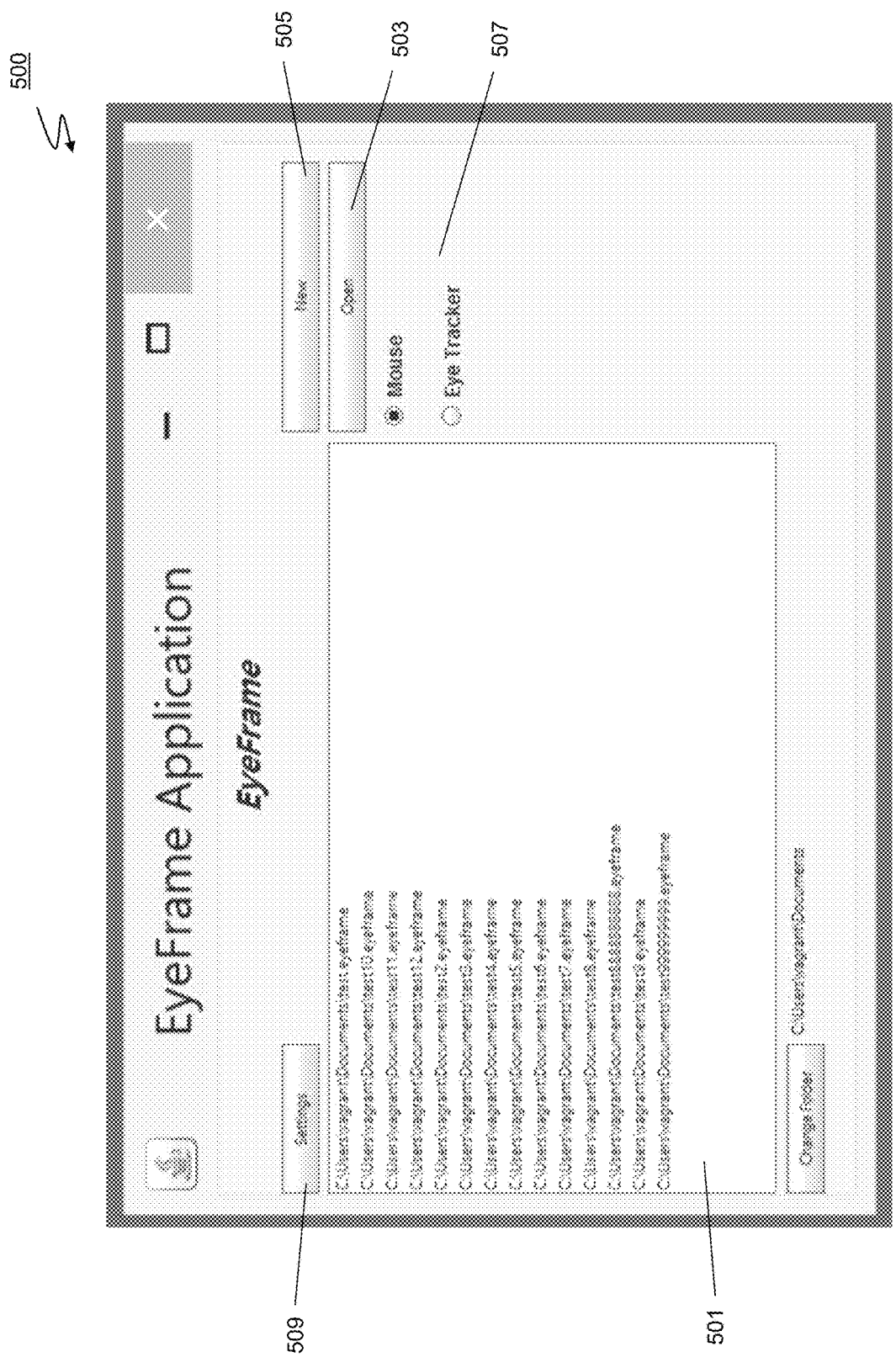
FIG. 2 illustrates a user interface of an application that may be used during the sensory cue program phase.

FIG. 2 illustrates a user interface 500 of an application that may be implemented to program the application for recording attention input data. As shown, an existing file may be opened by highlighting the existing file in the documents window 501 and selecting the button 503. If a new file is created (see FIG. 6), button 505 is selected. To select the available input device—mouse or eye tracker—, its corresponding icon bubble 507 is selected. Settings button 509 is chosen to select settings for the frames.

Figure 3:
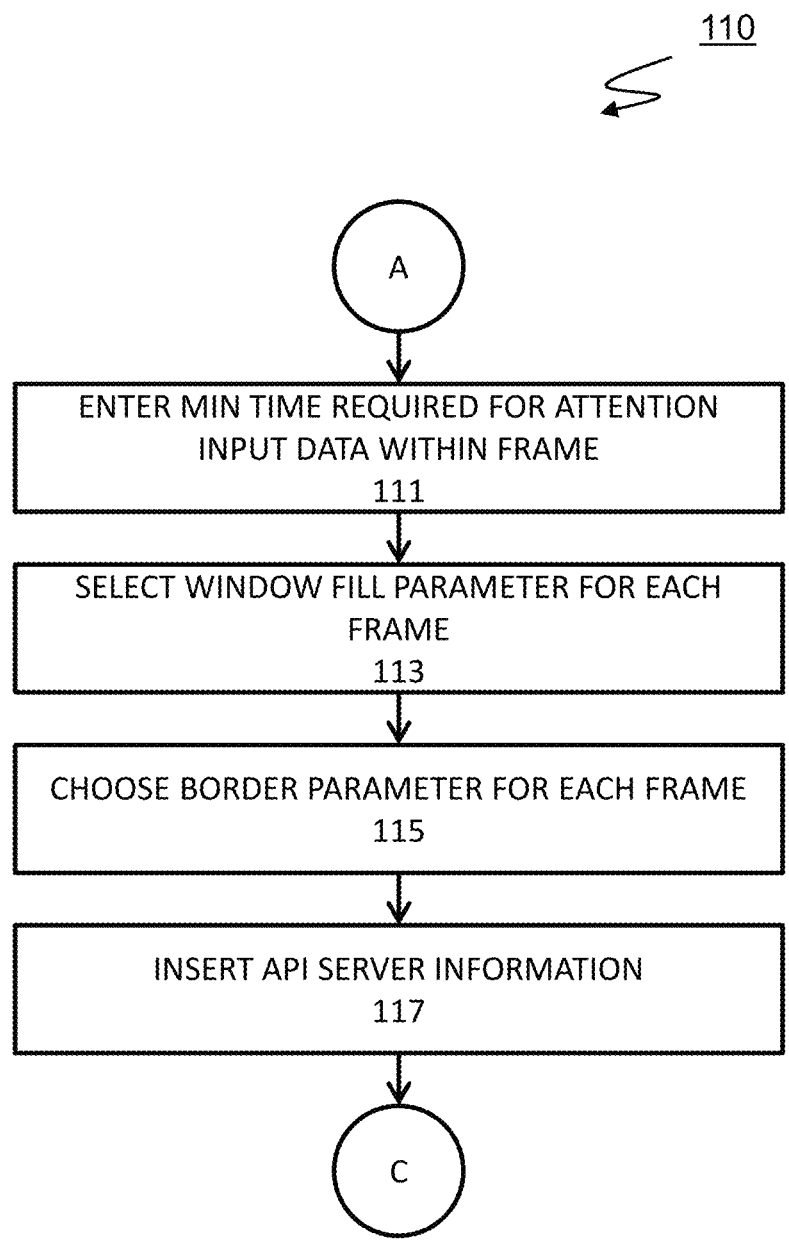
FIG. 3 illustrates a flow chart of method steps for defining settings for frames during the programming phase of the application.

FIG. 3 illustrates a flow chart 110 for directed to method steps for defining settings for the frames during the programming phase. At step 111, the minimum time threshold required to accept attention input data is entered. Attention input data is that which meets or exceeds the minimum threshold time, for example, a cursor within a frame as directed by the mouse input device controlled by a user or eye gaze within the frame as recorded by an eye tracker device.

Input data may be provided to the system using, for example, a computer mouse, a touch screen, a touch pad, a stylus, a keyboard. Frame parameters are then determined. At step 113, a window fill parameter for each frame is selected. At step 115, a border parameter is selected for each frame. If desired, API server information can be entered at step 117.

Figure 4:
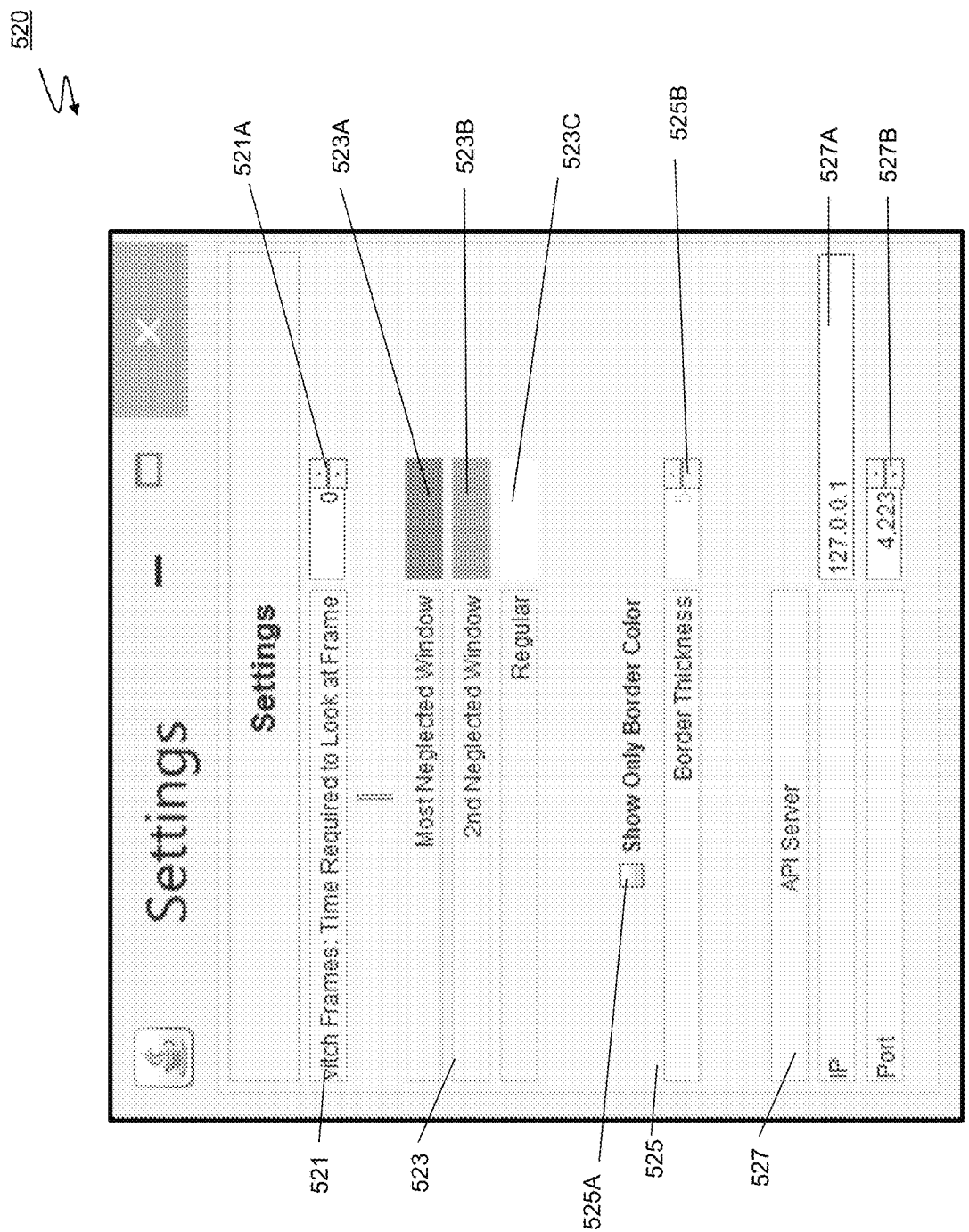
FIG. 4 illustrates a user interface that may be implemented to define settings for each frame.

FIG. 4 illustrates a user interface 520 for implementing the method of FIG. 3. Dependent upon the activity and related tasks, a time value is entered designating the minimum threshold time required to accept attention input data within the frame. For example, analysis of a MRI scan of the heart may require viewing for 7 seconds to register a user's gaze as attention input data. The minimum threshold time may be entered in measurements of second, minutes, hours, etc. and may be entered using a field 521 populated either using entry of a numerical value or scrolling +/− arrow controls 521A.

Window fill parameters 523 are defined using a field for each frame. Window fill parameters 523 include color and overlay in terms of opacity, translucency, and transparency. Different colors/overlay may be used to designate each type of frame: a first neglected frame, a second neglected frame and one or more regular (i.e., not neglected) frames. The neglected frames are determined based on the longest time since attention input data was recorded within the frame as compared to other frames (see FIG. 9). The most neglected frame is that with the largest time since last attended to, and the second most neglected frame is that with the second longest time internal since it was last attended to based on the accepted data. All other frames are considered normal or regular. In other words, the frame with the longest time since last accepted data of attention in comparison to all frames is the most neglected frame.

As shown, the most neglected frame is represented by field 523A directed to a dark opaque color. A second most neglected frame is represented by field 523B directed to a medium translucent color. Each regular frame is represented by field 523C directed to a light transparent color. It is contemplated that the colors may be reversed, for example, the first neglected frame represented by a light transparent color.

Figure 5:
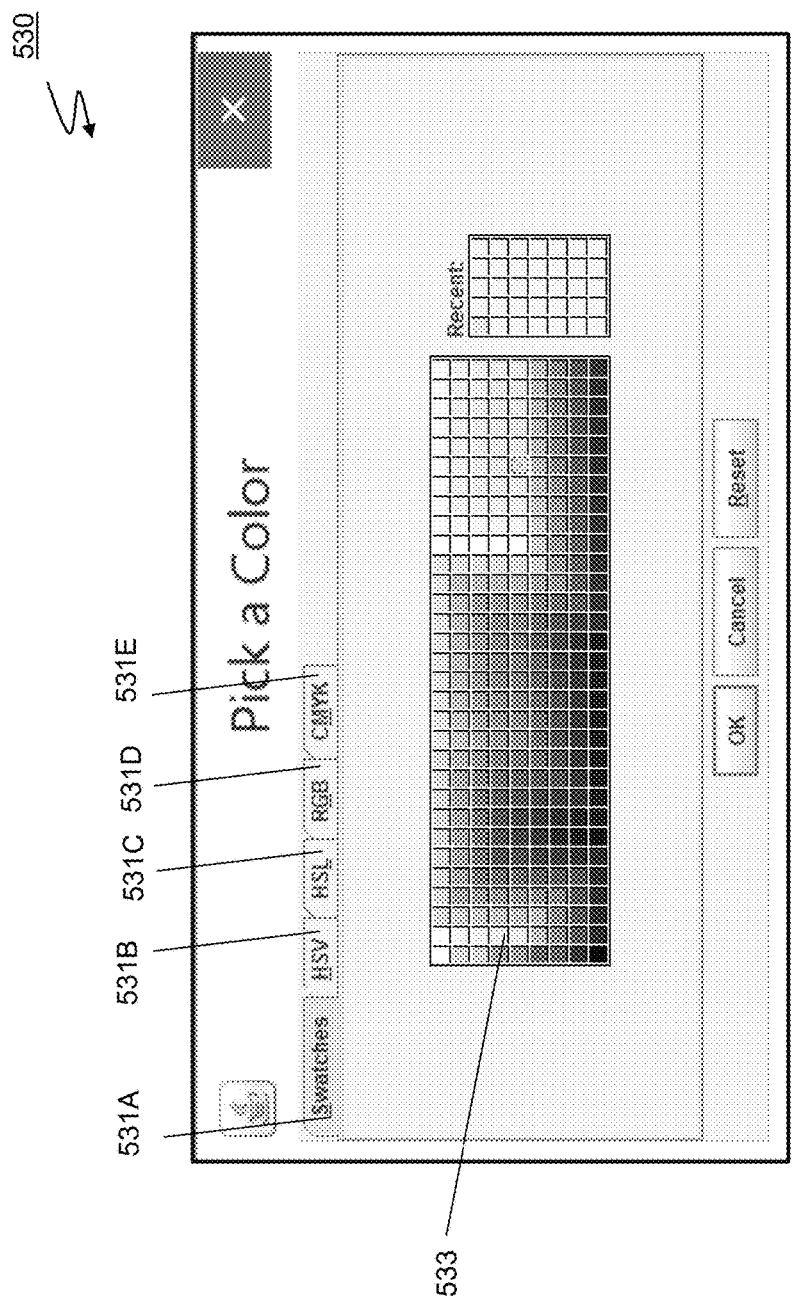
FIG. 5 illustrates a user interface that may be implemented to select color characteristics of each frame type.

Selecting any color field 523A, 523B, 523C may provide a pop-up screen display 530 as shown in FIG. 5. As shown in FIG. 5, the color for each type of frame—most neglected, second most neglected, regular—may be selected according to color tabs 531A, 531B, 531C, 531C, 531D, 531E. Tab 531A includes a swatch grid 533 of various colors. One box of the grid may be selected to designate the color of the frame type. The color for each frame type may also be designated using tab 531B directed to brightness in terms of hue, saturation, and value (HSV), tab 531C directed to lightness in terms of hue, saturation, and luminance (HSL), tab 531D directed to the additive color model red, green, blue (RGB), or tab 531E directed to the subtractive color model cyan, magenta, yellow, and black (CMYK).

Turning back to FIG. 4, border parameters 525 are chosen for the frame types. Border parameters may include, for example, border thickness and/or border style (solid, dashed, dotted). If desired, the frame may be illustrated by only a border through the selection of a toggle box 525A. Otherwise, the frame is illustrated by a window fill color, although it may be illustrated by both the border and window fill. The border thickness may be entered in measurements of millimeters, centimeters or any known measurement and may be entered using a field populated either using entry of a numerical value or scrolling +/− arrow controls 525B.

Application-programming interface (API) parameters 527 are selected to define a set of programming instructions and standards for accessing a web-based software application or tool. API server information can be inserted to point to a particular Internet Protocol (IP) address and port number to identify and locate the server from where the application is accessed. The IP address may be entered in a numerical format in field 527A and the port number entered either using entry of a numerical value or scrolling +/− arrow controls 527B.

In particular, the API server provides full control of the application including, for example, all options for settings for the frames, all saved sets of frames and all alerting frames. Although the API server provides most information to the application for recording attention input data to determine a neglected area of a screen display, it is contemplated that external applications and/or devices may be accessed to configure, start, and provide additional information to the application. It is also contemplated that external applications may communicate with the application asynchronously, with each handling a different portion of the application.

Figure 6:
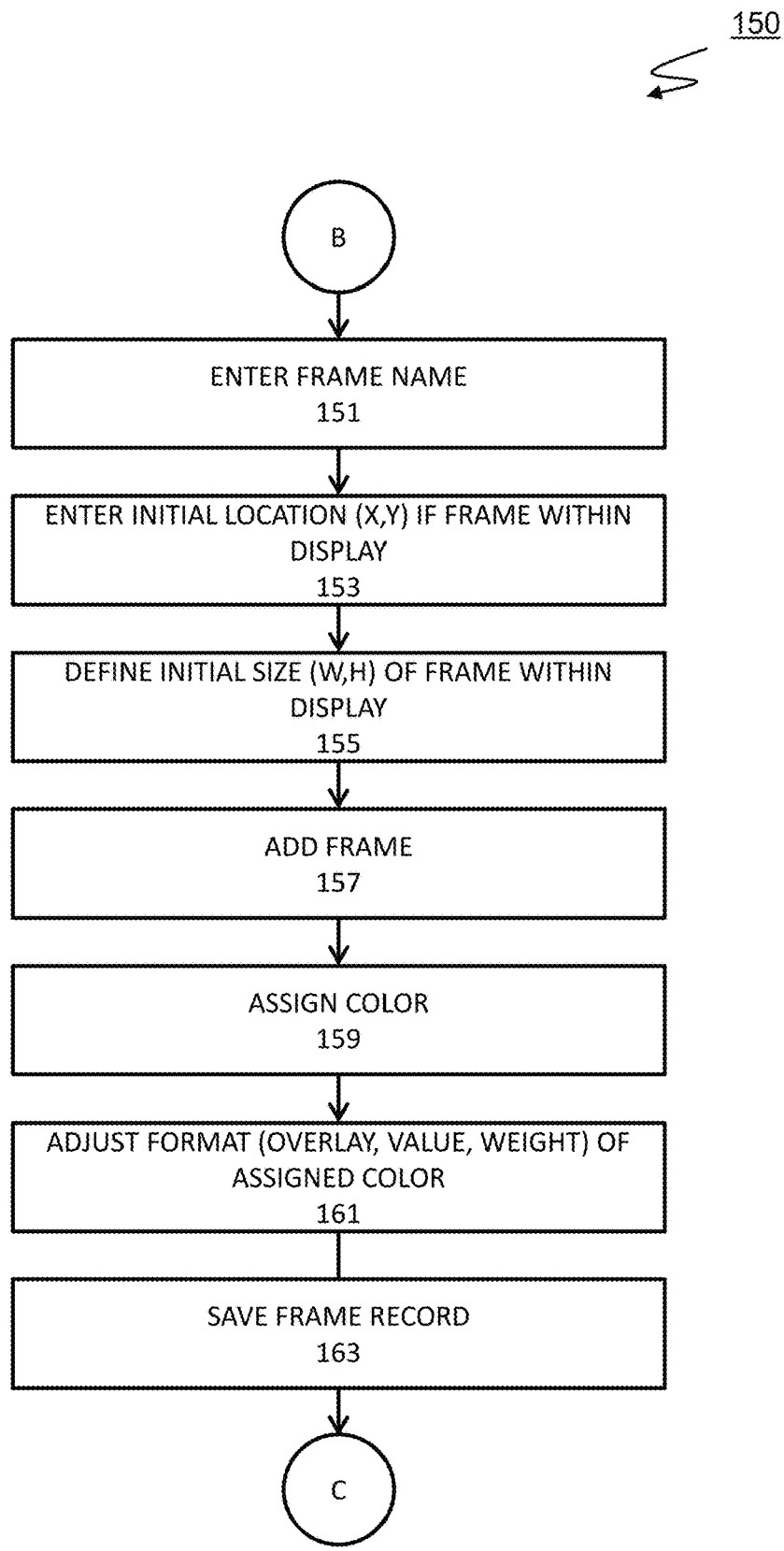
FIG. 6 illustrates a flow chart of method steps for adding frame records during the programming phase.

FIG. 6 illustrates a flow chart 150 of method steps for adding frame records to an application during the programming phase. The method of FIG. 6 may be implemented using the user interface 550 shown in FIG. 7.

As shown by step 151 in FIG. 6, a frame name is entered to identify the record. The initial location of the frame is entered according to x, y coordinates of the screen display at step 153. At step 155, the initial size of the frame is defined in terms of width and height dimensions. At step 157, the frame is added as a file to the server database. After the frame is added, the frame is assigned a color for easy identification at step 159. At step 161, the format—overlay, value, weight—of the frame color is adjusted. At step 163, the frame record is saved.

Figure 7:
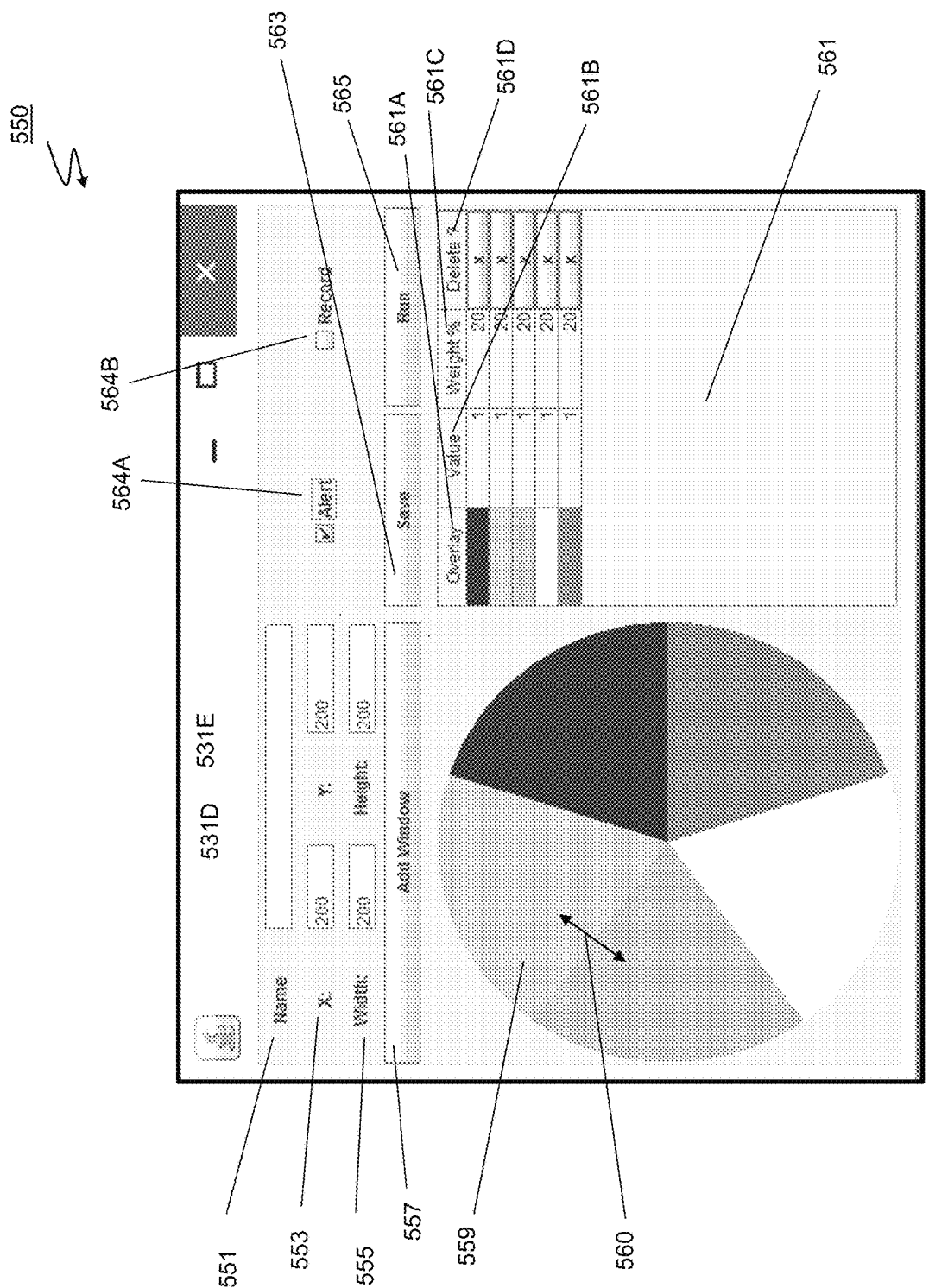
FIG. 7 illustrates a user interface of an application that may be implemented to add frame records.

FIG. 7 illustrates a user interface 550 for adding a frame record to an application for recording attention input data to determine a neglected area of a screen display. Field 551 is provided for identifying the record by name including, for example, an alphanumeric combination. The initial location of the frame is entered according to x, y coordinates 553. Values for the width dimension and height dimension for the initial size of the frame is defined in fields 555. Once the frame record is added as a file to the server database, such as by selecting button 557, the frame is automatically assigned a color for easy identification. The color identifying the frame appears in a pie chart diagram 559 and corresponding values for overlay 561A, weight value 561B, weight percentage 561C are presented in configuration table 561. Selecting the delete icon 561D removes the record from the database. In addition, the frame may appear on the screen display and can be manipulated by the cursor to be re-sized and moved. Accordingly, if the frame is re-sized or moved on the screen display, the x, y coordinates 553 of the location as well as the width and height dimensions 555 of the display 550 are each automatically updated. It is also contemplated that the pie chart diagram 559 may be manipulated to edit the related values of the configuration table 561. For example, a value may be entered in the weight value field 561B or arrow 560 can be manipulated to drag the edges of each pie slice to automatically adjust the weight percentage 561C of the frame as listed in the configuration table 561. Adjusting the weight percent increases or decreases the weight of the frame without adjusting the weights of all other frames. Hence, the total weight of all the frames may increase or decrease, instead of remaining the same. Button 563 is selected to save the set of frames as a file to the server database. Before executing the application, an alert indicator 564A and/or record indicator 564B may be selected. If the alert indicator 564A is selected, the frames are visible to the user during execution of the application. If the alert indicator 564A is deselected, the frames are not shown to the user. If the record indicator 564B is selected, a detailed recording of the frames' usage is gathered. If the record indicator 564B is deselected, the frames' usage during execution of the application is not recorded. The frame application is executed upon command, i.e., selection of graphic icon 565.

Figure 8:
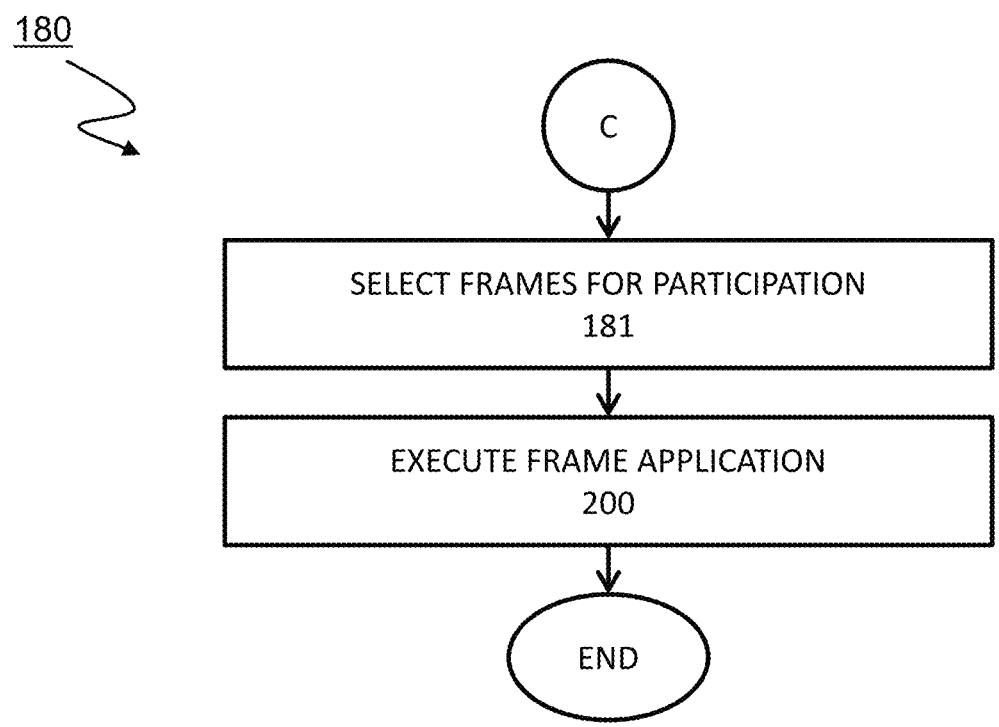
FIG. 8 is a flow chart including method steps for executing the frame application.

FIG. 8 is a flow chart 180 including method steps for executing the frame application. At step 181, a user selects the one or more frames from a set of frames stored on a database for participation during execution of the frame application. Upon selection of the frames for participation, the frame application is executed.

Figure 9:
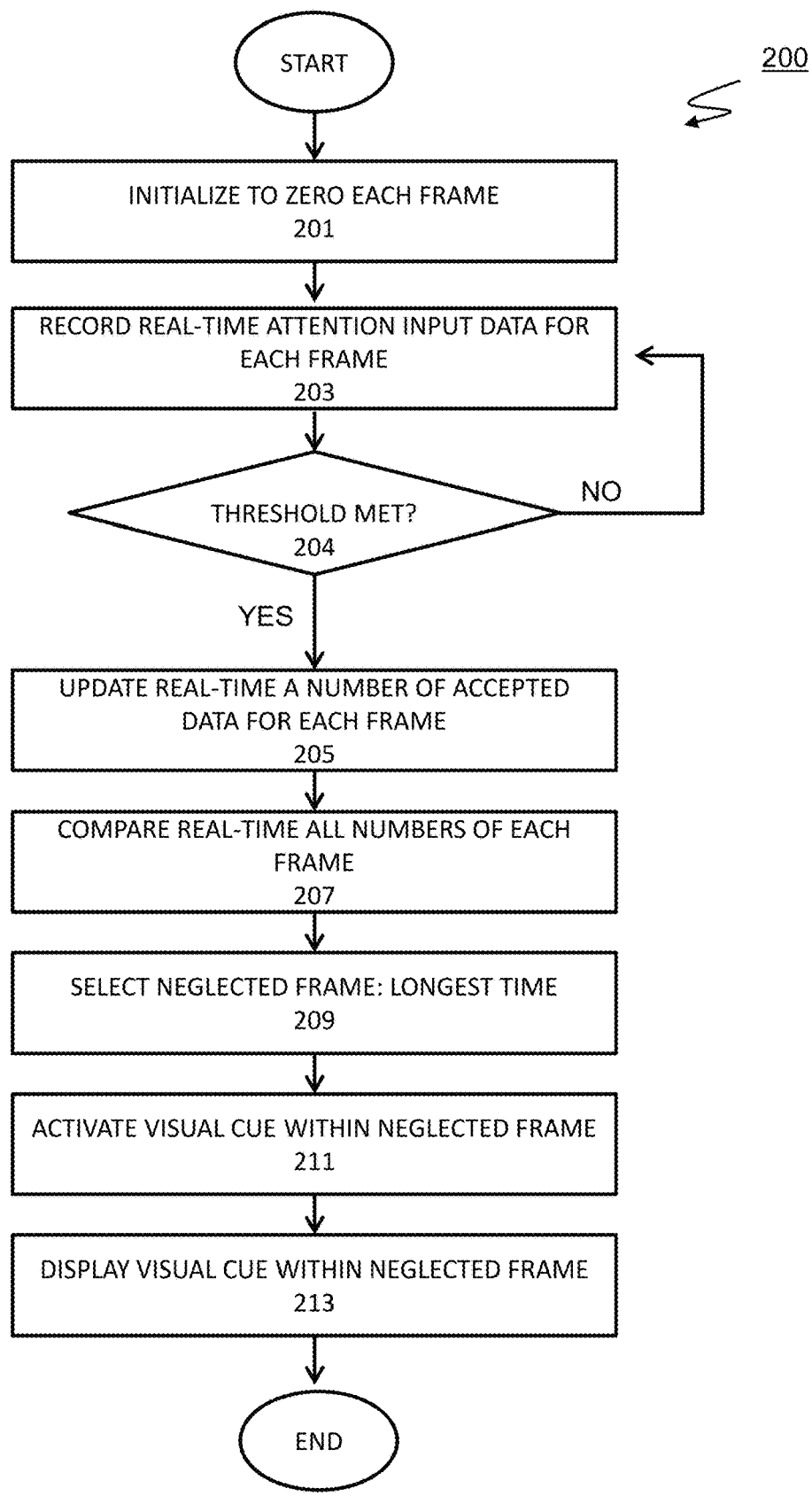
FIG. 9 is a flow chart of the method steps performed during an execution phase for determining real-time neglected areas of the screen display.

FIG. 9 illustrates a flow chart 200 of the method steps performed during the execution phase for determining real-time neglected areas of the screen display. At step 201, each frame is set to a zero value. At step 203, attention input data is recorded. Data is accepted automatically at step 204 when it meets the minimum threshold time (see FIG. 3). At step 205, a number value of accepted data for each frame is continuously evaluated in real-time. All number values of each frame are compared at step 207. Based on the comparison, neglected frames are selected at step 209. The most neglected frame selected is that with the longest duration of time measured from the previous acceptance of input data in comparison to the other frames and the second most neglected frame selected is that with the second longest duration of time measured from the previous acceptance of data. All other frames are considered normal or regular (i.e., not neglected). In other words, the frame with the longest duration since accepted data in comparison to all frames is the most neglected frame. At step 211, a visual sensory cue is activated for the neglected frames. At step 213, one or more visual cues are displayed according to each frame's defined parameters (see FIG. 3) drawing attention to the neglected areas.

Figure 10A:
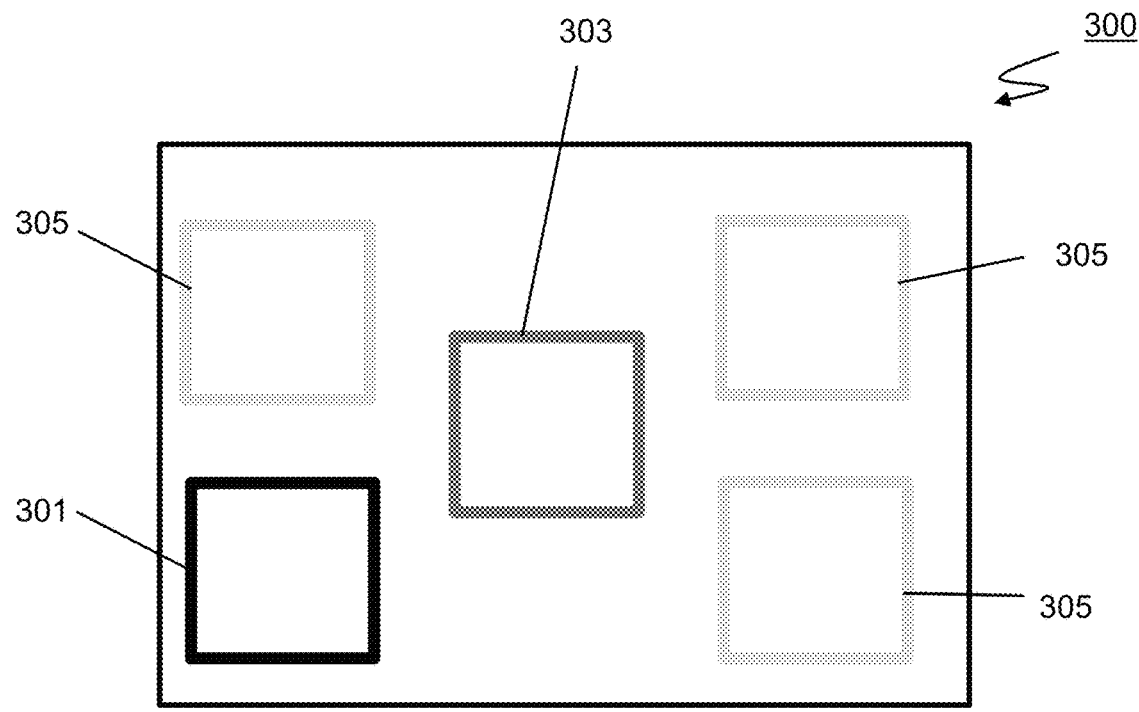
FIG. 10A illustrates a screen display during the execution phase of the frame application.
Figure 10B:
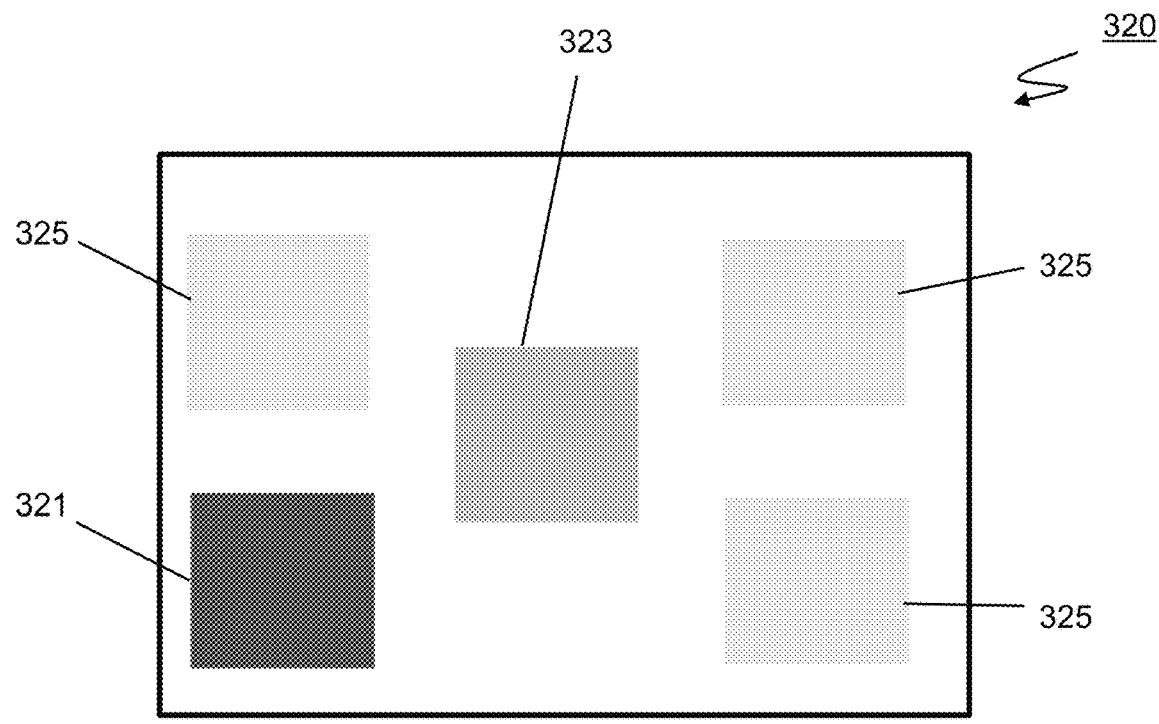
FIG. 10B illustrates a screen display during the execution phase of the frame application.
Figure 11:
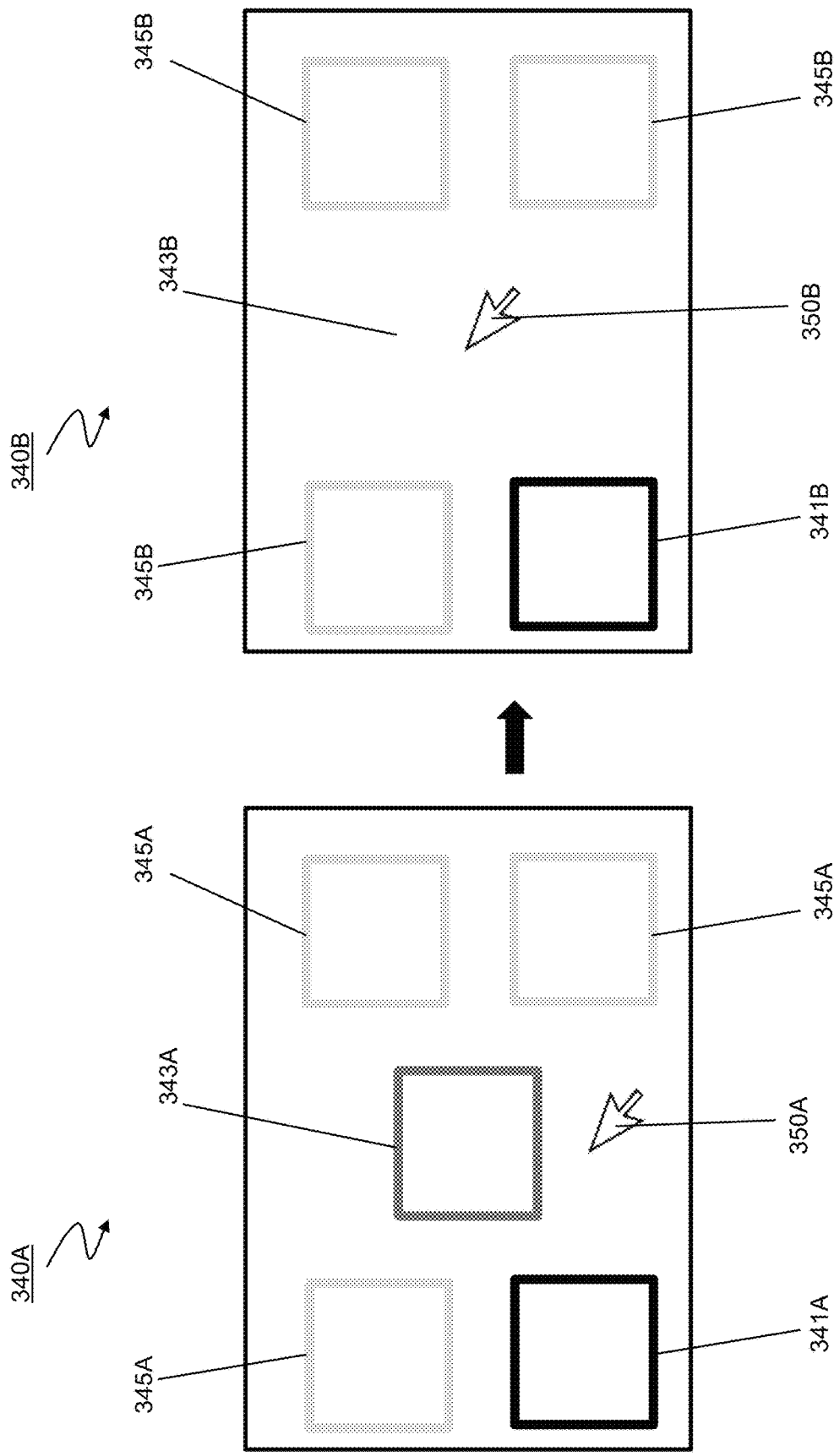
FIG. 11 illustrates a screen display during the execution phase of the frame application.

FIG. 10A, FIG. 10B, and FIG. 11 are directed to screen displays illustrating visual sensory cues or activation cues during execution of the frame application. According to FIG. 10A and FIG. 10B, an eye tracker device is used to determine a number of times attention input data is accepted within each frame, i.e., the eye tracker accepts a user's gaze that meets the minimum time threshold. The neglected frames are determined real-time as discussed in FIG. 9.

The screen display 300 in FIG. 10A illustrates all three frame types: first or most neglected frame 301, second neglected frame 303 and regular or "not neglected" frames 305. Only the border element of frames 301, 303, 305 is shown in FIG. 10A. The border element is illustrated as a solid, thin border as defined by the border parameters. FIG. 10A illustrates the frame as illustrated through the selection of toggle box 525A as described in FIG. 4. Without selection of of the toggle box 525A, the window element illustrates the frames as shown in the screen display 320 of FIG. 10B, although it is contemplated that the frames may be illustrated by both the border element and window element. FIG. 10B illustrates visual sensory cues during execution of the frame application in which the frames are presented according to the window parameters selected. As shown, neglected frame 321 is shown as a dark opaque color, second neglected frame 323 is shown as a medium translucent color and the normal frames 325 are shown a light transparent color.

FIG. 11 illustrates a screen display illustrating visual sensory cues or activation cues during execution of the frame application. According to FIG. 11, a cursor's position is used to determine a number of times attention input data is accepted within each frame, i.e., the cursor is located within a frame for a duration of time that meets the minimum time threshold. The cursor is positioned within a frame as directed by an input device controlled by a user. The neglected frames are determined real-time as discussed in FIG. 9. The attention input data is accepted within each frame provided the cursor remains within a frame to meet the minimum time threshold. FIG. 11 illustrates that frames may be hidden upon a user directing visual attention to that frame. As shown, screen display 340A includes neglected frames 341A, 343A and regular frames 345A. A cursor 350A shown at screen display 340A is moved so that the cursor 350B is positioned over the neglected frame 343B in screen display 340B. As a result, the frame 343B is hidden from the user when the user indicates that he or she is providing attention input data to that frame.

The system and methods of the invention were enabled in experiments further detailed and described in the papers: (1) Human Strategies for Multitasking, Search, and Control Improved via Real-time Memory Aid for Gaze Location, P. Taylor et. al, Front. ICT, 7 Sep. 2015 and (2) Eyeframe: Real-time Memory Aid Improves Human Multitasking Via Domain-General Eye Tracking Procedures, P. Taylor et al., Front. ICT, 2 Sep. 2015, both of which are incorporated by reference.

FIG. 12 illustrates a diagram of a system of which may be an embodiment of the invention. Computer system 600 includes an input/output interface 602 connected to communication infrastructure 604—such as a bus—, which forwards data such as graphics, text, and information, from the communication infrastructure 604 or from a frame buffer (not shown) to other components of the computer system 600. The input/output interface 602 may be, for example, a display device, a keyboard, touch screen, joystick, trackball, mouse, monitor, speaker, printer, Google Glass® unit, web camera, any other computer peripheral device, or any combination thereof, capable of entering and/or viewing data.

Computer system 600 includes one or more processors 606, which may be a special purpose or a general-purpose digital signal processor configured to process certain information. Computer system 600 also includes a main memory 608, for example random access memory (RAM), read-only memory (ROM), mass storage device, or any combination thereof. Computer system 600 may also include a secondary memory 610 such as a hard disk unit 612, a removable storage unit 614, or any combination thereof. Computer system 600 may also include a communication interface 616, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 608, secondary memory 610, communication interface 616, or a combination thereof, function as a computer usable storage medium, otherwise referred to as a computer readable storage medium, to store and/or access computer software including computer instructions. For example, computer programs or other instructions may be loaded into the computer system 600 such as through a removable storage device, for example, a floppy disk, ZIP disks, magnetic tape, portable flash drive, optical disk such as a CD or DVD or Blu-ray, Micro-Electro-Mechanical Systems (MEMS), nanotechnological apparatus. Specifically, computer software including computer instructions may be transferred from the removable storage unit 614 or hard disc unit 612 to the secondary memory 610 or through the communication infrastructure 604 to the main memory 608 of the computer system 600.

Communication interface 616 allows software, instructions, and data to be transferred between the computer system 600 and external devices or external networks. Software, instructions, and/or data transferred by the communication interface 616 are typically in the form of signals that may be electronic, electromagnetic, optical, or other signals capable of being sent and received by the communication interface 616. Signals may be sent and received using wire or cable, fiber optics, a phone line, a cellular phone link, a Radio Frequency (RF) link, wireless link, or other communication channels.

Computer programs, when executed, enable the computer system 600, particularly the processor 606, to implement the methods of the invention according to computer software including instructions.

The computer system 600 described may perform any one of, or any combination of, the steps of any of the methods according to the invention. It is also contemplated that the methods according to the invention may be performed automatically.

The computer system 600 of FIG. 12 is provided only for purposes of illustration, such that the invention is not limited to this specific embodiment. It is appreciated that a person skilled in the relevant art knows how to program and implement the invention using any computer system.

The computer system 600 may be a handheld device and include any small-sized computer device including, for example, a personal digital assistant (PDA), smart hand-held computing device, cellular telephone, or a laptop or netbook computer, hand held console or MP3 player, tablet, or similar hand-held computer device, such as an iPad®, iPad Touch® or iPhone®.

FIG. 13 illustrates an exemplary cloud computing system 700 that may be an embodiment of the invention. The cloud computing system 700 includes a plurality of interconnected computing environments. The cloud computing system 700 utilizes the resources from various networks as a collective virtual computer, where the services and applications can run independently from a particular computer or server configuration making hardware less important.

Specifically, the cloud computing system 700 includes at least one client computer 702. The client computer 702 may be any device through the use of which a distributed computing environment may be accessed to perform the methods disclosed herein, for example, a traditional computer, portable computer, mobile phone, personal digital assistant, tablet to name a few. The client computer 702 includes memory such as random-access memory (RAM), read-only memory (ROM), mass storage device, or any combination thereof. The memory functions as a computer usable storage medium, otherwise referred to as a computer readable storage medium, to store and/or access computer software and/or instructions.

The client computer 702 also includes a communications interface, for example, a modem, a network interface (such as an Ethernet card), a communications port, a PCMCIA slot and card, wired or wireless systems, etc. The communications interface allows communication through transferred signals between the client computer 702 and external devices including networks such as the Internet 704 and cloud data center 706. Communication may be implemented using wireless or wired capability such as cable, fiber optics, a phone line, a cellular phone link, radio waves or other communication channels.

The client computer 702 establishes communication with the Internet 704—specifically to one or more servers—to, in turn, establish communication with one or more cloud data centers 706. A cloud data center 706 includes one or more networks 710*a*, 710*b*, 710*c* managed through a cloud management system 708. Each network 710*a*, 710*b*, 710*c* includes resource servers 712*a*, 712*b*, 712*c*, respectively. Servers 712*a*, 712*b*, 712*c* permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software.

The cloud management system 708 can comprise a dedicated or centralized server and/or other software, hardware, and network tools to communicate with one or more networks 710*a*, 710*b*, 710*c*, such as the Internet or other public or private network, with all sets of resource servers 712*a*, 712*b*, 712*c*. The cloud management system 708 may be configured to query and identify the computing resources and components managed by the set of resource servers 712*a*, 712*b*, 712*c* needed and available for use in the cloud data center 706. Specifically, the cloud management system 708 may be configured to identify the hardware resources and components such as type and amount of processing power, type and amount of memory, type and amount of storage, type, and amount of network bandwidth and the like, of the set of resource servers 712*a*, 712*b*, 712*c* needed and available for use in the cloud data center 706. Likewise, the cloud management system 708 can be configured to identify the software resources and components, such as type of Operating System (OS), application programs, and the like, of the set of resource servers 712*a*, 712*b*, 712*c* needed and available for use in the cloud data center 706.

The invention is also directed to computer products, otherwise referred to as computer program products, to provide software to the cloud computing system 700. Computer products store software on any computer useable medium, known now or in the future. Such software, when executed, may implement the methods according to certain embodiments of the invention. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems (MEMS), nanotechnological storage device, etc.), and communication mediums (e.g., wired, and wireless communications networks, local area networks, wide area networks, intranets, etc.). It is to be appreciated that the embodiments described herein may be implemented using software, hardware, computer code, or combinations thereof.

The cloud computing system 700 of FIG. 13 is provided only for purposes of illustration and does not limit the invention to this specific embodiment. It is appreciated that a person skilled in the relevant art knows how to program and implement the invention using any computer system or network architecture.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A computer system method for providing one or more sensory cue to direct visual attention on a screen display, the method comprising:
   (a) defining an area on the screen display where attention will be measured;
   (b) programming sensory cues to estimate attention during a programming phase, the programming including:
      accessing a user interface for defining settings for each sensory cue;
      entering a minimum time threshold required to accept attention input data associated with each sensory cue;
      selecting parameters for each sensory cue;
      choosing sensory cues for participation; and
      defining an input device for acquiring attention input data; and
   (c) executing the sensory cues during an execution phase with respect to a frame or region, the executing including:
      (a) initializing each chosen sensory cue for each frame or region to a zero value;
      (b) recording real-time attention input data;
      (c) accepting the real-time attention input data if the minimum time threshold is met;
      (d) updating real-time a duration of time between accepted attention input data for each sensory cue in each frame or region;
      (e) comparing real-time all durations of time of all sensory cues within the frames or regions;
      (f) selecting the frame or region with the longest duration of time thereby demonstrating a measurement of attention and assigning a neglected status to that frame or region;
      (g) displaying an activation cue for visual attention in the frame or region on the screen display according to the selected parameters; and
      (h) repeating (b)-(g) until the execution phase ends.

2. The computer system method of claim 1 wherein the sensory cue is a visual sensory cue.

3. The computer system method of claim 2 wherein the visual sensory cue is a frame component including a window element and a border element.

4. The computer system method of claim 2 wherein the selecting includes:
   selecting a window fill parameter for each visual sensory cue; and
   selecting a border parameter for each visual sensory cue.

5. The computer system method of claim 4 wherein the window fill parameter is one or more selected from a group of: a color and an overlay including opacity, translucency, and transparency.

6. The computer system method of claim 5, further comprising selecting the color using a swatch grid.

7. The computer system method of claim 5, further comprising selecting the color using one or more models selected from the group comprising another group that includes:
   hue, saturation, value (HSV) model,
   hue, saturation, luminance (HSL) model,
   red, green, blue (RGB) model, and
   cyan, magenta, yellow, black (CMYK) model.

8. The computer system method of claim 4 wherein the border parameter is a border thickness, border style, or combination thereof.

9. The computer system method of claim 1 further comprising creating a frame or region record.

10. The computer system method of claim 9 wherein the creating includes:
    entering an initial location of the frame or region based on x, y coordinates of the screen display;
    defining an initial size and location of each frame or region based on a height dimension and a width dimension;
    assigning a color to the frame or region; and
    adjusting a color format of the assigned color, wherein the color format includes overlay, weight value, and weight percentage.

11. The computer system method of claim 1 wherein the attention input data includes eye gaze of the user, eye movement of the user, and device input according to movement of at least one input device by the user.

12. The computer system method of claim 11 wherein the at least one input device includes a computer mouse, touch screen, touch pad, stylus, keyboard, or combination thereof.

* * * * *

UNITED STATES PATENT AND TRADEMARK OFFICE
CERTIFICATE OF CORRECTION

PATENT NO.         : 10,732,784 B2
APPLICATION NO.    : 15/694709
DATED              : August 4, 2020
INVENTOR(S)        : Hava T. Siegelmann and Patrick Taylor Page 1 of 1

It is certified that error appears in the above-identified patent and that said Letters Patent is hereby corrected as shown below:

In the Claims

In Column 14, Claim 7, Line 30, delete "the group comprising"

Signed and Sealed this
Twenty-second Day of September, 2020

Andrei Iancu
*Director of the United States Patent and Trademark Office*